US008440630B2

(12) United States Patent
Noguchi et al.

(10) Patent No.: US 8,440,630 B2
(45) Date of Patent: May 14, 2013

(54) AKT ACTIVITY SPECIFICALLY INHIBITING POLYPEPTIDE

(75) Inventors: Masayuki Noguchi, Sapporo (JP); Futoshi Okada, Yamagata (JP); Makoto Hiromura, Kyoto (JP)

(73) Assignee: Japan Science and Technology Agency, Kawaguchi-Shi, Saitama (JP)

( * ) Notice: Subject to any disclaimer, the term of this patent is extended or adjusted under 35 U.S.C. 154(b) by 1749 days.

(21) Appl. No.: 10/583,058

(22) PCT Filed: Dec. 14, 2004

(86) PCT No.: PCT/JP2004/018646
§ 371 (c)(1),
(2), (4) Date: May 10, 2007

(87) PCT Pub. No.: WO2005/056594
PCT Pub. Date: Jun. 23, 2005

(65) Prior Publication Data
US 2012/0034651 A1 Feb. 9, 2012

(30) Foreign Application Priority Data

Dec. 15, 2003 (JP) ................................. 2003-416556
Apr. 28, 2004 (JP) ................................. 2004-134583

(51) Int. Cl.
| A61K 38/10 | (2006.01) |
| A61K 38/16 | (2006.01) |
| A61P 35/00 | (2006.01) |
| A61P 35/02 | (2006.01) |
| G01N 33/574 | (2006.01) |

(52) U.S. Cl.
USPC ....... 514/21.5; 514/21.3; 514/19.4; 514/19.6; 530/324; 530/326; 435/7.23

(58) Field of Classification Search .......................... None
See application file for complete search history.

(56) References Cited

U.S. PATENT DOCUMENTS 5,985,598 A 11/1999 Russo et al.
6,174,993 B1 * 1/2001 Ben-Sasson .................. 530/326

FOREIGN PATENT DOCUMENTS

| JP | 2002-500649 T | 1/2002 |
| JP | 500649 T * | 8/2002 |
| WO | WO 96/13514 | 5/1996 |
| WO | WO 98/53050 | 11/1998 |
| WO | WO 00/55169 | 9/2000 |

OTHER PUBLICATIONS

Fu 1994, Cancer Research, 54, 6297-6301.*
Narducci, 1997, Oncogene, 15, 919-926.*
Hiromura, JBC, 2004, 279, 53407-53418 (Mentioned in PTOL 413B).*

Office Action in related Chinese Application No. 200480037365.6 issued on Oct. 17, 2008.
English Translation of Office Action in related Chinese Application No. 200480037365.6 issued on Oct. 17, 2008.
Wang Hau—Zu, Gong Xing-Guo, "Progress in protein kinase B", *Chinese Journal of Pathophysiology*, 19(11):1521-1526 (2003). English Abstract provided.
Cui T. et al., "Angiotensin II Subtype 2 Receptor Activation Inhibits Insulin-Induced Phosphoinositide 3-Kinase And Akt And Induces Apoptosis In PC12W Cells", *Molecular Endocrinology*, vol. 16, No. 9, pp. 2113-2123, (2001).
French S. W. et al., "A Modeled Hydrophobic Domain On The TCL1 Oncoprotein Mediates Association With AKT At The Cytoplasmic Membrane", *Biochemistry*, No. 41, pp. 6376-6382 (2002).
Hiromura M. et al., "Inhibition Of Akt Kinase Activity By A Peptide Spanning The βA Strand Of The Proto-oncogene TCL1", *The Journal of Biological Chemistry*, vol. 279, No. 51, pp. 53407-53418, (Dec. 2004).
Martelli Am et al., "A New Selective AKT Pharmacological Inhibitor Reduces Resistance to Chemotherapeutic Drugs, TRAIL, All-Trans-Retinoic Acid, And Ionizing Radiation Of Human Leukemia Cells", *MTT Leukemia*, vol. 17, pp. 1794-1805 (2003).
Ming X. et al., "Rho GTPase/Rho Kinase Negatively Regulates Endothelial Nitric Oxide Synthase Phosphorylation Through The Inhibition of Protein Kinase B/Akt in Human Endothelial Cells", *Molecular and Cellular Biology*, vol. 22, No. 24, pp. 8467-8477, (Dec. 2002).
Noguchi M. et al., "Proto-oncogene TCL1: More Than Just A Coactivator For Akt", *The Faseb Journal*, vol. 21, pp. 2273-2284 (Aug. 2007).
Supplementary Partial European Search Report for the related European Application No. 04807007.2-1212, Completion of the European Search: Aug. 2, 2007; Date of Mailing Oct. 16, 2007.
Supplementary Partial European Search Report for the related European Application No. 04771321.9, Completion of the European Search: Nov. 20, 2007; Date of Mailing Nov. 30, 2007.
Marducci M. G. et al., "The Murine *TCL1* Ocogene: Embryonic And Lumphoid Cell Expression," *Oncogene*, No. 15, pp. 919-926, (1997).
Virgilio L. et al., "Identification Of The *TCL1* Gene Involved In T-cell Malignancies," *Proc. Natl. Acad. Sci. USA*, vol. 91, pp. 12530-12534, (Dec. 1994).
Stern M.H. et al., "MTCP-1: A Novel Gene On The Human Chromosome Xq28 Translocated To The T Cell Receptor α/δ Locus In Mature T Cell Proliferations," *Oncogene* No. 8, pp. 2475-2483, (1993).

(Continued)

*Primary Examiner* — Satyanarayana R Gudibande
(74) *Attorney, Agent, or Firm* — Locke Lord LLP

(57) ABSTRACT

The present invention is to provide a polypeptide specifically inhibiting the activity of Akt (Protein Kinase B), the DNA thereof, the antibody thereof, an inhibitor of Akt activity or an antitumor agent, and the like. The polypeptide comprises polypeptides (SEQ ID NO: 1, 3, 5, 7, and 9 of the sequence listing) that contain an amino acid sequence corresponding to any of the position of amino acid residue 10-24 of human TCL1, amino acid residue 8-22 of human TCL1B, amino acid residue 5-19 of human MTCP1, and amino acid residue 9-24 of mouse or rat TCL1; and the derivatives. Further, the present invention includes DNA encoding the polypeptide (SEQ ID NO: 2, 4, 6, 8 or 10 of the sequence listing), and the antibodies specifically binding to the polypeptides. The polypeptide of the present invention can be used for an inhibitor of Akt activity, an antitumor agent, or the like.

8 Claims, 13 Drawing Sheets

OTHER PUBLICATIONS

Coffer P.J. et al, "Protein Kinase B (c-Akt): A Multifunctional Mediator Of Phosphatidylinositol 3-kinase Activation," *Biochem. J.*, No. 335, pp. 1-13, (1998).

Datta S. R. et al. "Cellular Survival: A Play In Three Akts," *Genes and Development*, No. 13, pp. 2905-2927, (1999).

Brunet A. et al. "Akt Promotes Cell Survival by Phosphorylating And Inhibiting A Forkhead Transcript Factor," *Cell*, Vo. 96, pp. 857-868, (Mar. 1999).

Fruman D. A. et al. "Phosphoinositide Kinases," *Annu. Rev. Biochem.*, No. 67, pp. 481-507, (1998).

Künstle G. et al., "Identification Of Akt Association And Oligomerization Domains Of The Akt Kinase Coativator TCL1," *Molecular And Cellular Biology*, pp. 1513-1525, (Mar. 2002).

Laine J. et al., "The Protooncogene TCL1 Is An Akt Kinase Coactivator," Molecular Cell., vol. 6, pp. 395-407, (Aug. 2000).

Laine J. et al., "Differential Regulation Of Akt Kinase Isoforms By The Members Of The TCL1 Oncogene Family," *The Journal of Biological Chemistry*, vol. 277, No. 5, pp. 3743-3751, (Feb. 2002).

Obata T. et al., "Peptide And Protein Library Screening Defines Optimal Substrate Motifs for AKT/PKB," *The Journal of Biological Chemistry*, vol. 275, No. 46, pp. 36108-36115, (Nov. 17, 2000).

International Preliminary Report on Patentability in corresponding PCT Application No. PCT/JP2004/018646.

Narducci M. G. et al. "The murine TCL1 oncogene: embryonic and lymphoid cell expression," Oncogene, No. 15, pp. 919-926 (1997).

* cited by examiner

AKT ACTIVITY SPECIFICALLY INHIBITING POLYPEPTIDE

CROSS-REFERENCE TO A RELATED APPLICATION

This application is a National Phase Application under 35 U.S.C. §371 of International Application No. PCT/JP04/18646 filed on Dec. 14, 2004, which claims priority under 35 U.S.C. §119 (a)-(d) to Japanese Patent Application No. 2004-134583 filed on Apr. 28, 2004 and Japanese Patent Application No. 2003-416556 filed on Dec. 15, 2003, the entire contents of which are hereby incorporated by reference in their entirety.

TECHNICAL FIELD

The present invention relates to a polypeptide specifically inhibiting the activity of serine threonine kinase Akt (Protein Kinase B); a DNA encoding the peptide; a specific inhibitor of Akt activity or an antitumor agent, which contains the polypeptide as an active ingredient; and the like.

BACKGROUND ART

Akt kinase (Protein Kinase B: hereinafter referred to as Akt) is a serine threonine phosphorylation enzyme that was found in the beginning of the 1990s one after the other by following the homology between virus v-Akt. To date, it has been identified that there are three subtypes of the Akt. These molecules have around 80% homology, and have attracted attention from the beginning in relation to oncogenic transformation. In particular, it has been found and attracted attention that they play a central role to inhibit apoptosis in intracellular cytokine signaling (Genes & Dev., 13:2905-2927, 1999; Annu. Rev. Biochem, 67:481-507, 1998; Biochem. J, 335: 1-13, 1998).

This Akt has an approximate molecular weight of 57 kD, is selectively bound to inositol phosphate in the pleckstrin homology domain (PH domain); and has a function at the N-terminal, which mainly plays a role to define the localization to cell membranes. It also has a phosphorylation kinase domain at the c-terminal. It has been speculated that the binding of PIP3 and the like to PH domain by a signal from Phosphatidylinositol 3-kinase (PI3K) to translocate AKT molecules onto the membrane, and to alter the tertiary structure of Akt are involved in the activation.

Phosphorylations of the both two amino acids, threonine308 (Thr308) and serine473 (Ser473) have been considered to be essential for Akt activation. Wnile it has been known that Thr308 is phosphorylated by phosphoinositide dependent kinase (PDK1), the phosphorylation process of Ser473 has not been fully elucidated; it has been only speculated the possibility that some of uncertain molecules such as integrin linked kinase (ILK) or PDK2 are involved in the phosphorylation process. Further, recently the possibility of autophosphorylation for Ser473 phosphorylation has been reported.

It has known that the activated Akt promotes the phosphorylation of the molecules involved in the apoptosis inhibition. An amino acid sequence in the vicinity of serine/threonine, which is phosphorylated by this Akt, has been known as RXRXXS/T (J. Biol. Chem., 275: 36108-36115). The molecule such as BAD.Caspace 9.FKHRI (forkhead transcription factor) has the above amino acid sequence, and has been known as a substrate of Akt under physiological conditions. Inactive BAD is phosphorylated by Akt; binds to 14-3-3 protein in a phosphorylation-dependent manner; and liberates proteins such as active, Bcl-2 or Bcl-XL, which have apoptosis inhibitory action. It is thought that Akt plays a central role for apoptosis inhibitory control through these known functions and unexplained various targets (Cell, 96:857-868, 1999).

As described above, serine/threonine kinase Akt has a function to phosphorylate serine or threonine residue of intracellular protein specifically, and plays a role to mediate signal transduction to multi-organelle by the phosphorylation function. Further, the phosphorylation function of the Akt regulates a variety of intracellular mechanisms, and involved in the regulation of the various intracellular mechanisms such as, mitosis, cell growth, cell differentiation, control of lipid mentabolisn, immune response, inflammatory response, control of glycogen metabolism. At the same time, this means that the phosphorylation function of the Akt is involved in a wide range of various diseases and disorders such as cancer, obesity, autoimmune injury, inflammation and diabetes (type 2).

Recently, it has been reported that Akt activation is involved in breast cancer, lung cancer, prostate cancer, ovarian cancer, or hematological malignancies such as leukemia and lymphoid tumor (Annu. Rev. Biochem. 68, 965, 1999). As Akt activity is raised in these malignancies, Akt activation is considered to be a cause of these malignancies. In recent days, these serine/threonine kinase activities are modulated by using short peptides that are derivatives of the HJ loop of a serine/threonine kinase, with which treatments for diseases and disorders as described above have been attempted (published Japanese translation of PCT international publication No: 2002-500649).

On the one hand, TCL1 has been known as a protooncogene. TCL1 was noted that the activity is raised in human T cell prolymphocytic leukemia (T-PLL), and has been known to date that there are three similar subtypes (TCL1, MTCP1, TCL1b) (Oncogene, 8:2475-2483, 1993; Proc. Natl. Acad. Sci. USA, 91:12530-12534, 1994). It has been known that the expression was activated by translocation of these loci: 14q, 32, $\chi$28 to T cell receptor loci to develop human leukemia (T-PLL). However, it is a small protein of 13-16kD, and does not have the specific function structure that has been known to date, whose function has so far not been elucidated.

The expression of these molecules is comparatively limited under physiological conditions. TLC1 expression is limited to the lymphoid cells of T cells in an early differentiation (CD3-/CD4-/CD8-), and various B cells before the plasma cell differentiation. Further, although the details in the expression of MTCP1 under physiological conditions are unknown, it was identified from the recent analysis results of gene expression that the expression are induced in activated T cells. TCL1b is a recently cloned molecule and exists in the immediate vicinity of TCL locus. It is thought that there are five subtypes in mouse and is only one subtype in human. It has been reported that this gene expression has distinctly high expression in germinal cells in an early differentiation.

Genes of TCL1 are cloned, and a base sequence of 342 and an amino acid sequence of 113 are elucidated (U.S. Pat. No. 5,985,598).

However, functions of TCL1 have been unknown at all to date. The present inventors found that protooncogene TCL1 binds to Akt, from the search result of the protein molecules binding to Akt with the use of a library derived from human B cell by two-hybrid screen using a yeast to elucidate the process of Akt activation. That is, the present inventors indicated that TCL1 is bound to Akt, multimerized, and Akt of the multimer is activated; and found that TCL1 is the Akt coactivator promoting the Akt activation (Mol. Cell, 6:395-407, 2000). Further, the present inventors elucidated that TCL1 facilitated the Akt-mediated cell division, inhibition of apoptosis and the like, and is a predisposing factor for leukemia, tumor of human lymphatic system and the like. In subsequent studies, by coimmunoprecipitation assay using recombinant proteins in and out of cells, the present inventors indicated that TCL1 facilitated the polymerization among heterogeneous Akt molecules and phosphorylation of serine472/473 residues of Akt among heterogeneous Akt molecules; and elucidated the molecular mechanism that TCL1 activates the Akt (J. Biological Chemistry, 277[5], 3743-3751, 2002).

Further, the present inventors prepared an amino acid random library of TCL1 oncogene by applying PCR method and identified the amino acid sites required for the binding of Akt to TCL1 and the polymerization of TCL1, and moreover identified the mutated form of TCL1 which lacks dimerization or binding potency to Akt of TCL1. In addition, it was identified that the mutated form of TCL1 lacks Akt activation potency (both in vitro and in vivo), and loses various types of functions in TCL1 such as stabilization of mitochondrial outer membrane, inhibition of apoptosis, and nuclear translocation of Akt (Molecular and Cellular Biology, 22[5], 1513-1525, 2002). In other words, the present inventors found that protooncogene TCL1, whose function was unknown so far, is a co-activator of Akt, and is essential for the binding to Akt and the polymerization of TCL1-to-TCL1 when Akt activates.

Patent document 1: Published Japanese translation of PCT international publication No. 2002-500649
Patent document 2: Specification of U.S. Pat. No. 5,985,598
Nonpatent document 1: Genes & Dev., 13: 2905-2927, 1999
Nonpatent document 1: Annu. Rev. Biochem, 67: 481-507, 1998
Nonpatent document 1: Biochem. J, 335: 1-13, 1998
Nonpatent document 1: J. Biol. Chem., 275: 36108-36115
Nonpatent document 1: Cell, 96: 857-868, 1999
Nonpatent document 1: Oncogene, 8:2475-2483, 1993
Nonpatent document 1: Proc. Natl. Acad. Sci. USA, 91: 12530-12534, 1994
Nonpatent document 1: Mol. Cell, 6:395-407, 2000
Nonpatent document 1: J. Biological Chemistry, 277[5], 3743-3751, 2002
Nonpatent document 1: Molecular and Cellular Biology, 22[5], 1513-1525, 2002

DISCLOSURE OF THE INVENTION

Object to be Solved by the Present Invention

An object of the present invention is to provide a polypeptide specifically inhibiting the activity of serine threonine kinase Akt (Protein Kinase B); a DNA encoding the polypeptide; an antibody specifically binding to the polypeptide; a specific inhibitor of Akt activity or an antitumor agent, which contains the polypeptide as an active ingredient; and the like.

Means to Solve the Object

The present inventors elucidated that protooncogene TCL1, whose function had been unknown at all, directly binds to Akt that is involved in human malignancy and the like, promotes the activation of Akt, that is, is the co-activator of Akt, moreover, it is responsible for leukemia, tumor of human lymphatic system and the like. It was indicated that the mutated form of TCL1, which does not bind to Akt, lacks the Akt activation potency and loses various types of functions in TCL1 such as stabilization of mitochondrial outer membrane, inhibition of apoptosis, and nuclear translocation of Akt. From these serial studies; it was found that the position of an amino acid residue 10-24 in the amino acid sequence of TCL1 (human) is the binding site to Akt, and cell growth associated with Akt activation and the like are specifically inhibited by using a polypeptide sequence of the amino acid residue; and the present invention was led to complete.

Further, it was also identified that similar functions exist in the TCL1B and MTCP1 (human) having the similar functions to those of TCL1, and found that the cell growth associated with Akt activation inhibits at the positions of an amino acid residue 8-22 in amino acid sequence of TCL1B (human) and of an amino acid residue 5-19 in amino acid sequence of MTCP1 (human); and then the present invention was completed. Furthermore, in the present invention, it was also identified that the cell growth associated with Akt activation was inhibited at the positions of an amino acid residue 9-24 in amino acid sequence of mouse TCL1 and of an amino acid residue 9-24 in amino acid sequence of rat TCL1. Polypeptide in the present invention competitively inhibits the binding of phosphoinositide (phosphatidylinositol) to Akt.

In other words, the present invention comprises a polypeptide consisting of an amino acid sequence (SEQ ID NO: 1 of the sequence listing) corresponding to the position of an amino acid residue 10-24 in amino acid sequence of TCL1 (human), an amino acid sequence (SEQ ID NO: 3 of the sequence listing) corresponding to the position of an amino acid residue 8-22 in amino acid sequence of TCL1B (human), an amino acid sequence (SEQ ID NO: 5 of the sequence listing) corresponding to the position of an amino acid residue 5-19 in amino acid sequence of MTCP1 (human), an amino acid sequence (SEQ ID NO: 7 of the sequence listing) of the position of an amino acid residue 9-24 in amino acid sequence of TCL1 (mouse), and an amino acid sequence (SEQ ID NO: 9 of the sequence listing) of the position of an amino acid residue 9-24 in amino acid sequence of TCL1 (rat), and specifically inhibiting Akt activity, and DNA (SEQ ID NO: 2, 4, 6, 8 or 10 of the sequence listing) encoding the polypeptide.

Further, the present invention comprises a polypeptide derivative consisting of an amino acid sequence wherein one or several amino acids are deleted, substituted or added in an amino acid sequence of the polypeptides, and specifically inhibiting Akt activity; and a DNA encoding the sequences, or DNA that hybridizes with DNA in the sequences under stringent conditions and specifically inhibits Akt activity. Furthermore, the present invention includes a method for producing a polypeptide of the present invention by incorporating the DNA into an expression vector, constructing a recombinant expression vector, and introducing the recombinant vector into a host cell to be expressed.

Further, the present invention includes an antibody that specifically binds to the polypeptide specifically inhibiting the Akt activity of the present invention; moreover, includes utilization of specific inhibitor of Akt activity that contains a polypeptide of the present invention as an active ingredient, and of antitumor agent that contains the polypeptides as an active ingredient for prevention and treatment of malignancy and the like. Furthermore, the present invention includes a method for specifically inhibiting Akt activity by introducing the DNA encoding a polypeptide of the present invention into living cells to express the polypeptide.

That is, specifically, the present invention relates to (1) a polypeptide specifically inhibiting Akt activity, which consists of an amino acid sequence indicated in SEQ ID NO: 1, 3, 5, 7 or 9 of the sequence listing; and (2) a polypeptide consisting of an amino acid sequence wherein one or several amino acids are deleted, substituted or added in the amino acid sequence indicated in SEQ ID NO: 1, 3, 5, 7 or 9 of the sequence listing, and specifically inhibiting Akt activity.

The present invention also relates to (3) a gene DNA encording a following protein (a) or (b): (a) a polypeptide consisting of an amino acid sequence indicated in SEQ ID NO: 1, 3, 5, 7 or 9; (b) a polypeptide consisting of an amino acid sequence wherein one or several amino acids are deleted, substituted or added in the amino acid sequence indicated in SEQ ID NO: 1, 3, 5, 7 or 9, and specifically inhibiting Akt activity; (4) a DNA consisting of a base sequence indicated in SEQ ID NO: 2, 4, 6, 8, or 10; or part or whole of these sequences, and encoding a polypeptide that specifically inhibits Akt activity; and (5) a DNA hybridizing with the DNA according to "4" under stringent conditions, and encoding a polypeptide that specifically inhibits Akt activity.

The present invention further relates to (6) a recombinant expression vector, which is constructed by integrating a DNA encoding the polypeptide that specifically inhibits Akt activity according to any one of "3"-"5" into a gene expression vector; (7) a method for producing a polypeptide that specifically inhibits Akt activity wherein the recombinant expression vector according to "6" is introduced into a host cell and expressed; (8) an antibody which is induced by using a polypeptide indicated in SEQ ID NO: 1, 3, 5, 7 or 9 of the sequence listing and specifically binds to the polypeptide; (9) the antibody according to "8" wherein the antibody is a monoclonal antibody; and (10) the antibody according to "8" wherein the antibody is a polyclonal antibody.

The present invention still further relates to (11) a specific inhibitor of Akt activity, wherein the polypeptide according to "1" or "2" is an active ingredient; (12) the specific inhibitor of Akt activity according to "11", wherein the polypeptid is a sequence of an amino acid residue 10-24 of an amino acid sequence for human TCL1 protein; (13) the specific inhibitor of Akt activity according to "11", wherein the polypeptide is a sequence of an amino acid residue 8-22 of an amino acid sequence for human TCL1B protein; (14) the specific inhibitor of Akt activity according to "11", wherein the polypeptid is a sequence of an amino acid residue 5-19 of an amino acid sequence for human MTP1 protein; (15) the specific inhibitor of Akt activity according to "11", wherein the polypeptide is a sequence of an amino acid residue 9-24 of an amino acid sequence for mouse TCL1 protein; (16) the specific inhibitor of Akt activity according to "11", wherein the polypeptide is a sequence of an amino acid residue 9-24 of an amino acid sequence for rat MTP1 protein; and (17) the specific inhibitor of Akt activity according to any one of "11"-"16", wherein specific inhibition of Akt activity is the inhibition of binding of phosphoinositide to Akt.

Furthermore, the present invention relates to (18) an antitumor agent wherein the polypeptide according to "1" or "2" is an active ingredient; (19) the antitumor agent according to "18", wherein the antitumor agent is an agent for prevention or treatment of malignancy; (20) the antitumor agent according to "19", wherein treatment of malignancy is prevention or treatment of breast cancer, lung cancer, leukemia or lymphoid tumor; and (21) a method for specifically inhibiting Akt activity by introducing a DNA encoding the polypeptide that specifically inhibits Akt activity according to any one of "3"-"5" into living cells to express the polypeptide.

Effect of the Present Invention

Oncogene TCL1 is a co-activator of Akt (serine threonine phosphorylation enzyme: Protein Kinase B), and the TCL1 directly binds to Akt to promote the activation of Akt. In the present invention, polypeptides in the present invention enable its utilization as a specific inhibitor of Akt activity, by finding that the position binding to Akt in the amino acid sequence of the TCL1 is specified, and the polypeptides consisting of an amino acid sequence of the positions of the TCL1, TCL1B and MTCP1 that bind to Akt specifically inhibits the Akt activity. To date, a specific peptide inhibitor of Akt has been unknown, therefore, a polypeptide of the present invention can be expected the utilization thereof as an entirely new Akt activity inhibitor.

Further, Akt is an intracellular signaling molecule that plays a central role for inhibiting apoptosis. Akt is activated in many cancer cells, and apoptosis is impaired. As a result, apoptosis is decreased; cells are abnormally proliferated, and cancer is developed. Akt has been known to be a central molecule regulating apoptosis, and is an important subject of study; however, agents specifically inhibiting a central molecule Akt in apoptosis inhibitory mechanism have not been developed yet. Specific inhibitor of Akt activity in the present invention is involved in mechanism that contributes to cancer development such as apoptosis regulation, and leads to development of agents for prevention or treatment of malignancy in a background of AKT activation by overexpression of TCL1 gene or abnormality of cancer suppressor gene PTEN. As the Akt activity involved in malignancies such as breast cancer, lung cancer, prostate cancer, ovarian cancer, and hematological malignancy such as leukemia or lymphoid tumor; specific inhibitors of Akt activity in the present invention can be used as an antitumor agent (anticancer agent) for prevention or treatment of various human malignancies caused by activation of the Akt kinases.

BEST MODE OF CARRYING OUT THE INVENTION

Figure 1:
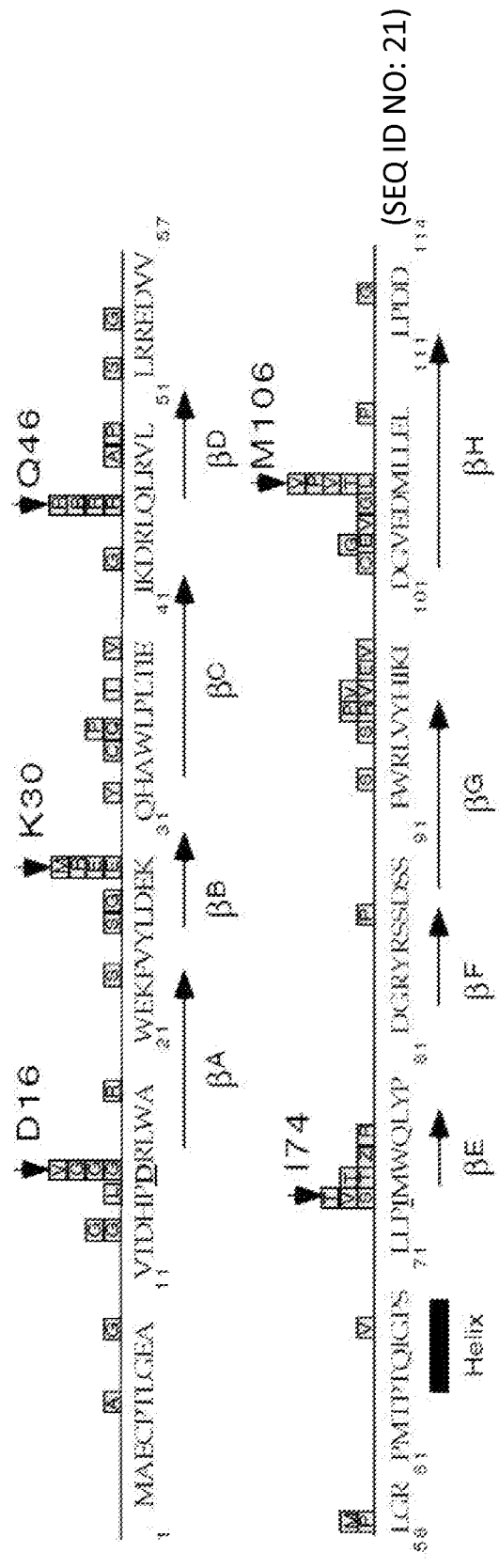
FIG. 1 is a set of pictures showing 10 clones of amino acid substitution indicating low interaction (8 h positive [+]) with Akt that was constructed and observed in experiments of the examples of the present invention, displaying amino acid sequence of TCL1 side-by-side.

The present invention comprises polypeptides: an amino acid sequence of amino acid residue 10-24 in human TCL1 oncogene, an amino acid sequence of amino acid residue 8-22 in human TCL1B, an amino acid sequence of amino acid residue 5-19 in human MTCP1, an amino acid sequence of amino acid residue 9-24 in mouse TCL1, and an amino acid sequence of amino acid residue 9-24 in rat TCL1, which are specifically inhibits Akt activity; and the amino acid sequences are indicated in SEQ ID NO: 1, SEQ ID NO: 3, SEQ ID NO: 5, SEQ ID NO: 7 and SEQ ID NO: 9 of the sequence listing. Further, the present invention comprises polypeptide derivatives consisting of an amino acid sequences wherein one or several amino acids are deleted, substituted or added in the amino acid sequences of the polypeptides, and specifically inhibiting Akt activity. DNA sequences encoding a polypeptide that consists of an amino acid sequence of amino acid residue 10-24 in Human TCL1 oncogene, an amino acid sequence of amino acid residue 8-22 in human TCL1B, or an amino acid sequence of amino acid residue 5-19 in human MTCP1; an amino acid sequence of amino acid residue 9-24 in mouse TCL1; or an amino acid sequence of amino acid residue 9-24 in rat TCL1; are indicated in SEQ ID NO: 2, SEQ ID NO: 4, SEQ ID NO: 6, SEQ ID NO: 8, and SEQ ID NO: 10 of the sequence listing. The present invention includes a DNA encoding a polypeptide that hybridizes with DNA of the sequences under stringent conditions and specifically inhibits Akt activity.

The polypeptide in the present invention can be synthesized by known method for polypeptide synthesis based on the structure of the polypeptide that consists of amino acid sequences indicated in SEQ ID NO: 1, SEQ ID NO: 3, SEQ ID NO: 5, SEQ ID NO: 7 or SEQ ID NO: 9 of the sequence listing; and further, can be produced by genetic manipulation with the use of a DNA sequence encoding the polypeptide. A DNA sequence of the entire gene in Human TCL1 oncogene and an amino acid sequence of a protein encoded by the gene are disclosed in U.S. Pat. No. 5,985,598, and the sequences of the gene and protein can be accessed from a database of GenBank by accession number: X82240 and CAA57708. In addition, a vector incorporated a full-length gene (cDNA and genome DNA) of TCL1 is respectively deposited at acceptance number: 75923 and 75924 as a deposit of microorganism according to Budapest Treaty on the International Recognition of the Deposit of Microorganisms for the Purposes of Patent Procedure at a depository institution in USA, American Type Culture Collection (ATCC). Further, a DNA sequence of mouse TCL1 gene and an amino acid sequence of a protein encoded by the gene, a DNA sequence of rat TCL1 gene and an amino acid sequence of a protein encoded by the genes, can be accessed from a database of NCIB by accession numbers NP_033363 and XP_345720 respectively.

A DNA sequence of the entire gene in TCL1B and an amino acid sequence of a protein encoded by the gene are disclosed in a reference (Proc. Natl. Acad. Sci. U.S.A., 96(6), 2949-2951, 1999), and can be accessed from a database of NCBI by accession number: AF_110465. Further, a DNA sequence of the entire gene in MTCP1 and an amino acid sequence of a protein encoded by the gene are disclosed a in reference (Oncogene 8 (9), 2475-2483, 1993), can be accessed from a database of NCBI by accession number: BC_002600.

A polypeptide in the present invention can be obtained by genetic manipulation performing the following step: producing DNA from an information as the above DNA sequences using synthesis method, or slicing out the DNA of the present invention from a source of TCL1 genes such as the above by using restriction enzyme; incorporating the gene into an appropriate expression vector; and introducing the recombinant vector into host cells to express the polypeptide. A variety of polypeptide derivatives in the present invention can be produced by the following steps: producing DNA of a base sequence encoding the polypeptide; constructing an expression vector by using the DNA; and introducing the expression vector into appropriate known host cells to express the polypeptide. Mutation of DNA sequence encoding a variety of polypeptide derivatives can be conducted by known genetic engineering gene mutation procedure.

To produce a polypeptide in the present invention by genetic manipulation, incorporating a DNA encoding the polypeptide into a known expression vector, constructing a recombinant expression vector, and introducing the vector into host cells to express the polypeptide can be performed. Introduction of the recombinant expression vectors into host cells can be performed with the use of appropriate known methods. For example, as for a host cell of prokaryote, *E coli, Bacillus subtilis* and *Pseudomonas* strains can be exemplified; as for a vector when using the prokaryote as host cells, a vector of *E coli* strains or the like such as pUC19, pBR322 and pBR327 can be used; as for a promoter, tryptophan promoter, PL promoter, lac promoter or tac promoter can be exemplified; as for a marker gene, ampicillin-resistant gene, tetracycline-resistant gene or the like can be used.

As for host cells of eukaryotic microorganism, yeast is widely used in general; as for a vector, for example, YRp7 and the like may be used. When using cultured cells of higher animals as host cells, COS cell, CHO cell (Chinese hamster ovary cell) and the like can be used. As for a promoter, for example, adenovirus-2 major late promoter, SV40 early promoter, SV40 late promoter, and a promoter from cytomegalovirus or Rous sarcoma virus; as for a marker gene, for example, neomycin-resistant gene, methotrexate-resistant dihydrofolate reductase (DHR) gene and the like; can be used. Furthermore, as for host cells, an insect cell such as BmN4 cell, Sf9 cell and Sf21 cell can be used.

In the present invention, by using a polypeptide of the present invention such as a polypeptide consisting of an amino acid sequence of amino acid residue 10-24 in human TCL1, the binding of Phosphoinositide (Phosphatidylinositol) are inhibited, and as a consequence, Akt (protein Kinase B) activity, cell growth, and anti-tumor effects can be obtained. For this peptide, administration as a recombinant protein, and a method of administration using a virus vector or a mammalian expression vector, can be considered. Induction method for peptide by fusion method with TAT peptide (part of HIV virus protein) can be also used. Moreover, electroporation, and intracellular induction methods that are pharmacologically possible, can be used. Peptide modification in the sense of peptide stabilization, PEG (polyethylene Glycol), FCR (FC Receptor), and production of fusion peptide with other peptide, can be used.

The present invention includes DNA encoding a polypeptide that hybridizes with a DNA sequence encoding a polypeptide consisting of an amino acid sequence of amino acid residue 10-24 in human TCL1 (a base sequence indicated in SEQ ID NO: 2 of the sequence listing), a DNA sequence encoding a polypeptide consisting of an amino acid sequence of amino acid residue 8-22 in human TCL1B (a base sequence indicated in SEQ ID NO: 4 of the sequence listing), a DNA sequence encoding a polypeptide consisting of an amino acid sequence of amino acid residue 5-19 in human MTCP1 (a base sequence indicated in SEQ ID NO: 6 of the sequence listing), a DNA sequence encoding a polypeptide consisting of an amino acid sequence of amino acid residue 9-24 in mouse TCL1 (a base sequence indicated in SEQ ID NO: 8 of the sequence listing), a DNA sequence encoding a polypeptide consisting of an amino acid sequence of amino acid residue 9-24 in rat TCL1 (a base sequence indicated in SEQ ID NO: 10 of the sequence listing), under stringent conditions and specifically inhibits Akt activity.

As for the conditions in the following phrase, "hybridizes . . . under stringent conditions", for example, hybridization at 42° C. and washing treatment at 42° C. with a buffer containing 1×SSC, 0.1% SDS, and preferably hybridization at 65° C. and washing treatment at 65° C. with a buffer containing 0.1×SSC, 0.1% SDS can be exemplified. Further, as for factors affecting the stringency of hybridization, there are a variety of factors other than the above temperature conditions; therefore, those in the art can conduct a stringency equivalent to the above exemplified stringency of hybridization using a variety of factors in combination.

The present invention includes an antibody specifically bound to a polypeptide that specifically inhibits the Akt activity of the present invention. As for the antibody, monoclonal antibody and polyclonal antibody can be exemplified. The antibody can be produced by ordinary method with the use of a polypeptide of the present invention as an antigen. It can be considered that the antibody of the present invention specifically inhibits the binding of TCL1, TCL1B or MTCP1 to Akt by specifically binding to TCL1, TCL1B or MTCP1 at the Akt-binding site. Further, the antibody of the present invention can be used to detect the diseases involved in TCL1, TCL1B or MTCP1 gene in tissue cells, serum and the like, by using antigen-antibody reaction with TCL1, TCL1B or MTCP1 polypeptide. In immunological measurement by using the antibody of the present invention, for example, known immunological measurement such as RIA assay, ELISA assay and fluorescent antibody method can be used.

In the present invention, a specific inhibitor of Akt activity uses a polypeptide of the present invention as an active ingredient, and an antitumor agent uses the polypeptide as an active ingredient for prevention and treatment of malignancy and the like. To use a polypeptide of the present invention as an active ingredient for specific inhibitor of Akt activity, and for an antitumor agent of prevention and treatment for malignancy and the like, the polypeptide can be used alone or by adding various mixture ingredients: pharmaceutically acceptable ordinary carriers, binding agent, stabilizing agent, excipient, diluent, pH buffer agent, disintegrating agent, solubilizer, solubilizing agent, isotonic agent and the like for formulation. These specific inhibitors of Akt activity and the prevention or treatment agent for malignancy and the like can be administered orally or parenterally. That is, ordinary administration formulations to use, for example, powder, granule, capsule, syrup, suspension and the like can be administered orally, or, for example, solution, emulsion, suspension and the like can be administered parenterally by injection, and moreover, spray formulation can be administered into nostril.

When a polypeptide of the present invention specifically inhibiting Akt activity is used for prevention/treatment of cancer and the like, a polypeptide specifically inhibiting Akt activity can be directly inoculated into cancer cells by using a reagent without cytotoxicities such as Chariot (Active Motif), which forms noncovalent complexes with macromolecules such as proteins, peptides or antibodies, alters structures of polypeptide, and can deliver polypeptide molecules into cells. In addition, the doses can be appropriately selected by depending on disease type, body weight of patient, administration method, and the like. As for a subject of the administration of a specific inhibitor for Akt activity or of an antitumor agent in the present invention, prevention or treatment for various diseases caused by Akt activation can be exemplified, especially prevention or treatment for malignancies such as breast cancer, lung cancer, prostate cancer, ovarian cancer, and hematological malignancy such as leukemia or lymphoid tumor can be exemplified.

In the present invention, by introducing the DNA encoding a polypeptide that specifically inhibits Akt activity of the present invention, into living cells to express the polypeptide, the Akt activity can be specifically inhibited. As for an expression vector in animal cells for introducing the DNA encoding a polypeptide that specifically inhibits Akt activity, into living cells, any vector can be used as long as the DNA encoding the above polypeptide of the present invention is integrated into a vector for animal cells, as for the vector for animal cells, the expression system is not especially limited as long as the DNA encoding the above polypeptide of the present invention can be expressed in host cells. For example, expression systems derived from chromosome, episome and virus; for example, vectors derived from bacterial plasmid, yeast plasmid, papovavirus such as sv40, vaccinia virus, adenovirus, fowlpox virus, pseudorabies virus, lentivirus and retrovirus: vectors derived from bacteriophage, transposon and the combination of those; for example, vectors derived from genetic components of plasmid and bacteriophage such as cosmid and phagemid, can be exemplified.

These expression systems not only cause the expression but also may contain regulatory sequences regulating the expressions. Further, in an expression vector for animal cells of the present invention, liposomes are also included. In these vectors for animal cells, an adenovirus vector is especially preferable in terms of safety and utility. In prevention and treatment for cancer and the like, administering directly at lesion sites (in situ) is preferable, for example, when using an adenovirus expression vector, the vector suspension can be directly inoculated into the lesion site such as cancer tissues. Further, when using a liposome holding the DNA encoding a polypeptide that specifically inhibits the Akt activity of the present invention, the liposome suspension can be directly inoculated into the lesion site such as cancer tissues.

The present invention will be explained in detail in the following by referring to the examples, but the technical scope of the present invention will not be limited to these.

Example 1

Identification of a Binding Sequence of Akt and TCL1

The interaction of an amino acid partial mutation TCL1 clone with Akt was examined by using yeast two-hybrid screening and semiquantitative β-Gal assay (MOLECULAR AND CELLULAR BIOLOGY, March 2002, P. 1513-1525).

TCL1 (Human) Amino Acid Random Mutation Library Screening for Identification of the Akt-TCL1 Binding Site (Materials and Methods)
1. TCL1 Library A full length of human TCL1 in pGAD424 (Clontech) was amplified by PCR with the use of a primer comprising 5'-CCACCAAACCCAAAAAAAGAGATCGAATTCATG (SEQ ID NO: 11) and 5'-ATTCATAGATCTCTGCAGGTC-GACGGATCCTCA (SEQ ID NO: 12), and a random TCL1 amino acid library was produced.

2. Production of Amino Acid Mutant Forms of TCL1

An amino acid-substituted mutant form of TCL1 (D16G, K30M, Q46R, I74V, M106V, 36-38A, or 36A/38Δ) was produced by PCR with the use of the following primer, and native and mutated forms were subcloned into the vector expressing pGAD424 (Clontech), pME18SHA (Mol. Cell 6:395-407), or pCMV Flag (Kodak).

Primers used are as follows (mutated codons are shown in lower-case letters): 5'-ATG GCC GAG TGC CCG ACA CTC GGG GAG GCA GTC ACC GAC CAC CCG GGC CGC CTG TGG GCC (SEQ ID NO: 13) for D16G; 5'-GTG TAT TTG GAC GAG ATG CAG CAC GCC TGG CTG (SEQ ID NO: 14) for K30M; 5'-G ATA AAG GAT AGG TTA CGG TTA CGG GTG CTC TTG (SEQ ID NO: 15) for Q46R; 5'-CCA AGC CTG CTG CCT GTC ATG TGG CAG CTC TAC (SEQ ID NO: 16) for I74V; 5'-ATC ATC GGA TCC TCA GTC ATC TGG CAG CAG CTC GAG AAG CAC GTC CTC C (SEQ ID NO: 17) for M106V; 5'-CAG CAC GCC TGG CTG GCC GCG GCC ATC GAG ATA AAG GAT (SEQ ID NO: 18) and a reverse complementary sequence for 36-38A; and 5'-GCC TGG CTG GCC TTA ATC GAG ATA (SEQ ID NO: 19) and a reverse complementary sequence for 36A/38Δ. Mutated positions of an amino acid-substituted mutant form of TCL1 (D16G, K30M, Q46R, I74V, M106V, 36-38A, or 36A/38Δ) are shown in FIG. 1.

3. Yeast Two-Hybrid Screening

Screening was performed by yeast two-hybrid system for detection of protein interaction to detect interaction of TCL1 with Akt protein.

Y190 cells (Clontech), by using lithium acetate method; and human Akt2 (Akt2/PAS2-1) and TCL1 random library, in accordance with the previous report (Mol. Cell 6:395-407; Proc. Natl. Acad. Sci. USA 94:11534-11539); were expressed in yeast. In the presence of 3-amino-1,2,4-triazole (SIGMA), around 104 clones from cDNA library were screened. β-galactosidase (β-Gal) activity in His+ colony was measured by using filter-lift assay. Yeast clones were classified into clone categories: 3 h-positive [++], 8 h-positive [+], and 24 h-negative [−] by the intensity of β-Gal. Ten clones were selected from the each category for sequencing of the nucleotide.

4. Quantitative β-Gal Assay

Y190 cells (Clontech) were expressed in yeast together with TCL1 of wild-type, D16G, K30M, Q46R, I74V, or M106V by using Akt2/PAS2-1, with the use of pGAD424 (Clontech) vector. TCL1 mutant was produced by using PCR-based site-directed mutagenesis and/or Quikchange kit (Stratagene). Liquid β-Gal assay was performed for quantitative determination of binding intensity by using ONPG (O-nitrophenyl-β-D-galactoppyranoside; Sigma) (Mol. Cell 6:395-407). The indicated values were determined by western blotting analysis (GAL4 activation domain antibody [Ab]: Clontech), and normalized by expressing transformant in each yeast.

Experiment and Results

Random TCL1 library was produced by PCR-mediated random mutation to determine the amino acid residues required for Akt-TCL1 binding. Each occurrence of the substituted DNA nucleotide was 1.4% for dATP, 3.8% for dTTP, 4.0% for dGTP, and 1.4% for dCTP. The total frequency of nucleotide substitution in this library was 2.7%, and the insertion-deletion frequency was 0.09%. The library size was around $2.5 \times 10^4$. The substituted positions were dispersed over 90% or more of the total TCL1 molecules in the sequenced 25 sample clones.

Next, a yeast two-hybrid screening was performed to examine the interaction of each clone with Akt2. Yeast clones were classified into three categories based on the blue-color intensity expressed in β-Gal lifting assay β-Gal positive [++] at 3 h, β-Gal positive [+] at 8 h, and negative [−]). Nucleotide sequences of the 10 clones in each category were determined. A ++clone included wild-type TCL1, or the mutants at P5, P15, D43, L45, P61, M75 and D88 positions; did not affect β-Gal activity, and its residue did not react to Akt interaction. The observed 10 clones of amino acid substitution indicating low interaction (8 h positive [+]) with Akt, and amino acid sequence of TCL1 were displayed side-by-side (FIG. 1).

Figure 2:
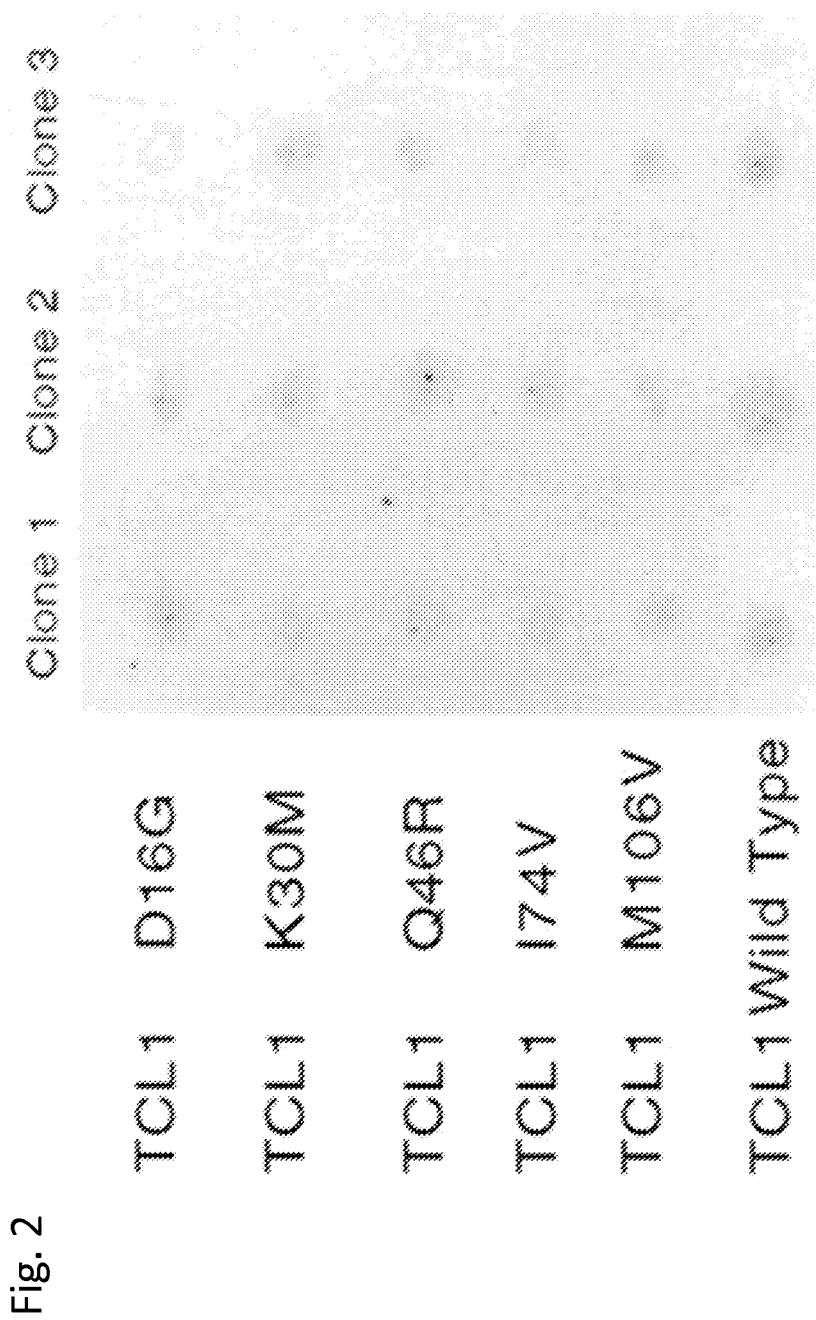
FIG. 2 is a set of pictures showing the results of β-Gal lifting assay with the use of TCL1 mutants (D16G, K30M, Q46R, I74V, or M106V) induced by site-directed mutagenesis and wild-type TCL1, in experiments of the examples of the present invention.
Figure 3:
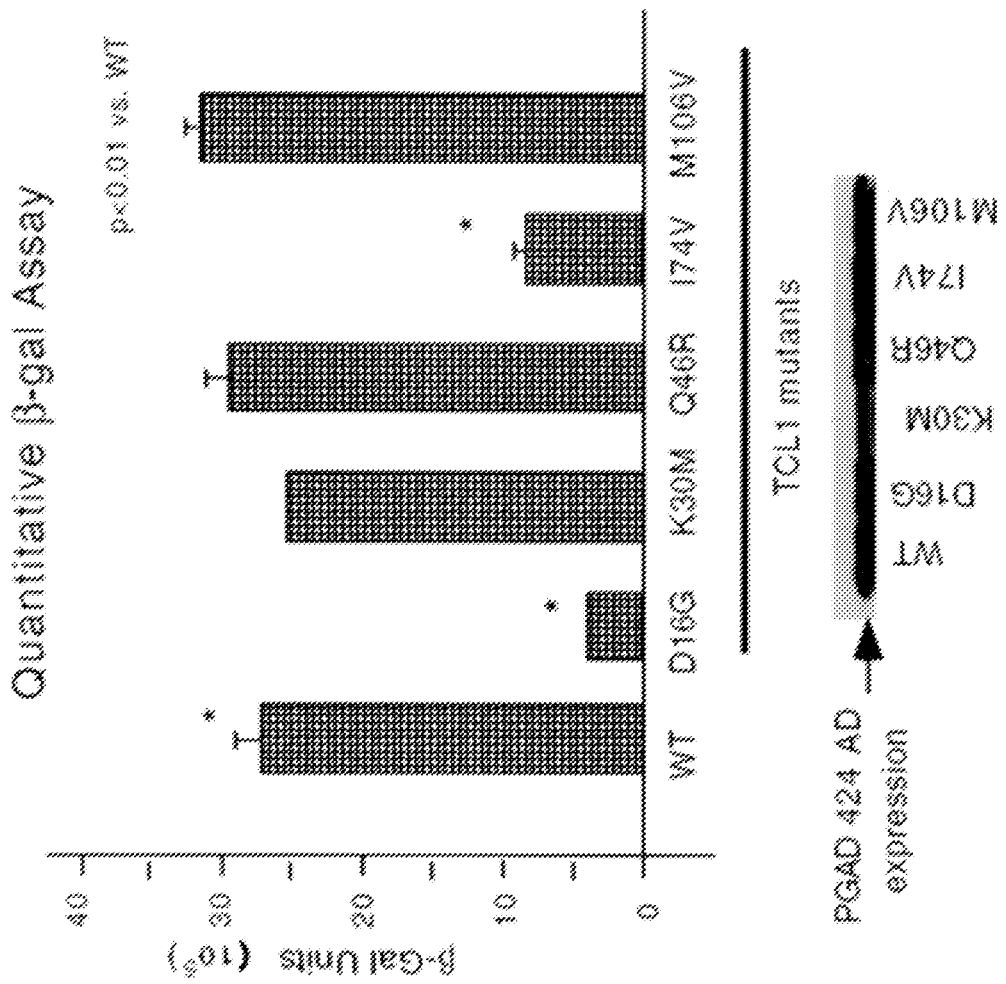
FIG. 3 is a set of pictures showing the results of quantitative liquid β-Gal assay with the use of TCL1 mutants (D16G, K30M, Q46R, I74V, or M106V) induced by site-directed mutagenesis and wild-type TCL1, in experiments of the examples of the present invention.

Deposition of substitution was evidently found in specific residues of these clones. The substitution was found in at least one of amino acids in D16, K30, Q46, I74 and M106, in 9 clones out of 10 clones. Negative clone [−] was not involved in nucleotide insertion, insertion associated with large deletions, structural shift, and/or a large amount of mutants. Therefore, further analysis was eliminated. The present inventors hypothesized that clones showed Akt low interaction must contain an amino acid residue required for Akt-TCL1 interaction. Therefore, each mutant (D16G, K30M, Q46R, I74V or M106V) was produced in TCL1 by using a site-directed mutagenesis method. In D16G and I74V mutants, the bindings to the Akt mutant were resulted in dramatic decrease in D16G and I74V, as shown in β-Gal lifting assay (FIG. 2) and quantitative liquid β-Gal assay (FIG. 3).

(Association with Akt and TCL1 Homodimer, Required for TCL1-Induced Akt Activation)

Figure 4:
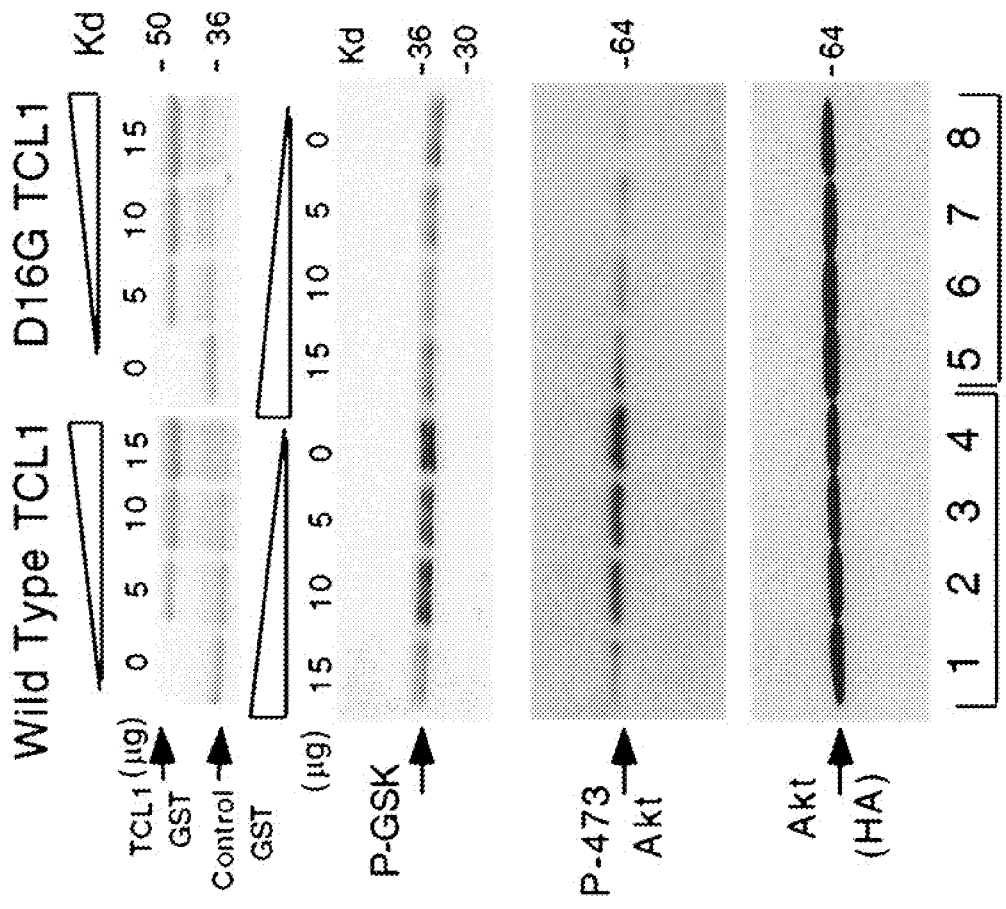
FIG. 4 is a set of pictures showing the results of in vitro kinase assay for wild-type TCL1 to examine the association of Akt with TCL1 homodimer, which is required for TCL1-induced Akt activation, in experiments of the examples of the present invention.
Figure 5:
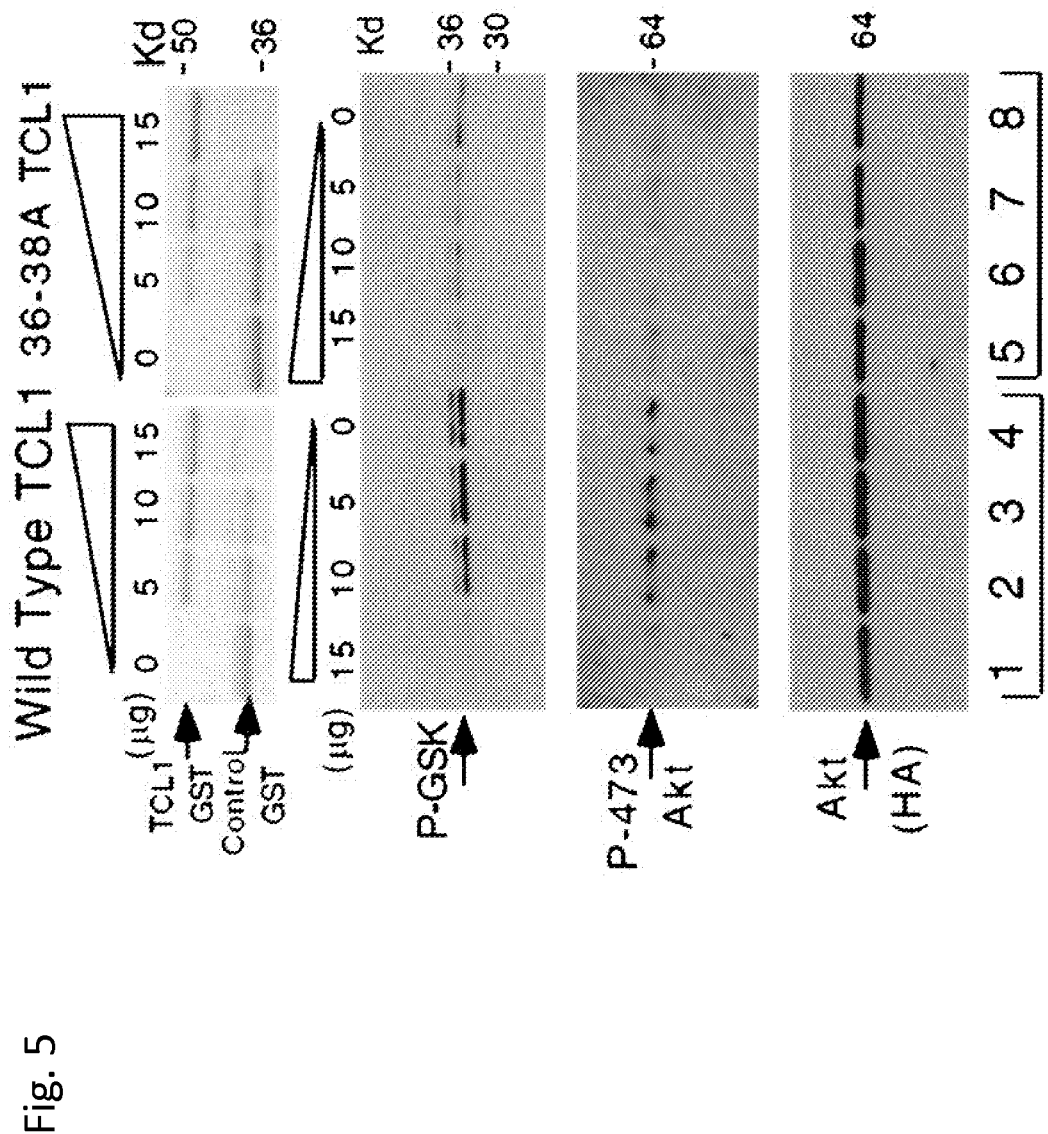
FIG. 5 is a set of pictures showing the results of in vitro kinase assay for TCL1 mutants (36-38A TCL1) to examine the association of Akt with TCL1 homodimer, which is required for TCL1-induced Akt activation, in experiments of the examples of the present invention.

Wild-type TCL1 showed an increase in Akt kinase activity in an in vitro kinase assay. This was predominantly correlated with Akt Ser-473 phosphorylation levels. However, D16G TCL1 did not affect the Akt kinase activity even though in a dose escalation experiment (FIG. 4). D16G TCL1 did not affect both GSK-3α phosphorylation and Akt Ser-473 phosphorylation. D16G TCL1 was evaluated by Akt kinase activity. Similarly, 36-38A TCL1 that binds to Akt but not form homodimer (in an in vitro kinase assay, determined by phosphorylated GSK-3α and Ser-473 Akt) was not able to enhance the Akt kinase activity (FIG. 5). These indicated that the mutated form of TCL1, which does not bind to Akt, lacks Akt activation potency (both in vitro and in vivo).

(Production of a Binding Sequence Between Akt and TCL1)

From the result of previous analysis in TCL1 crystal structure (Molecular and Cellular Biology, March 2002, p. 1513-1525), it was thought that D16 exists at initial position of the first β sheet, and Akt kinase binds on a surface made by the first β sheet and the forth β sheet. Based on these series of studies, it was thought that amino acid binding to Akt in TCL1 protein molecules, amino acid residue sequence 10-24 (Table 1) of TCL1 oncogene in the vicinity of the 16 residue (Asparadic Acid), binds to Akt and can be an inhibitor of Akt activation.

Example 2

Assay for 10/24 Peptide of TCL1

1. Cell Growth Test by Using MTT Assay

Figure 6:
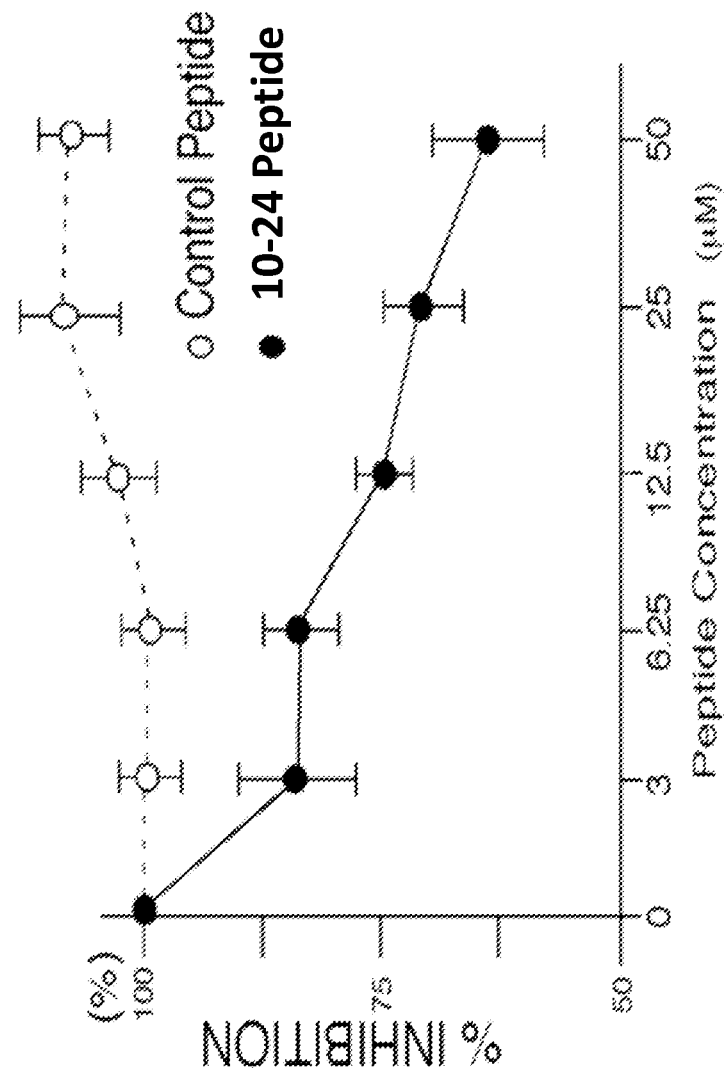
FIG. 6 is a picture showing the results of MTT assay with the use of the peptide consisting of the sequence of 10-24 amino acid residues of TLC1 oncogene to identify that the cell growth associated with AKT activation is specifically inhibited, in experiments of the examples of the present invention.

Cell growth test was performed by using MTT assay. That is, in experiments of cell growth by using WST-8 reagent [2-(2-methoxy-4-nitrophenyl)-3-(4-nitrophenyl)-5-(2,4-disulfophenyl)-2H-tetrazolium, monosodium salt] (347-07621, Dojin, Kumamoto, Japan) assay, it was identified that amino acid residue sequence 10-24 peptide (NH2-AVTDHPDRL-WAWEKF-COOH) (SEQ ID NO: 1) of this TLC1 oncogene specifically inhibits cell growth associated with AKT activation (FIG. 6).

In this method, 10/24 peptide was pre-treated at 0-50 μM concentration in cell growth test by using T4 cell lines without stimulation, 48 hours later the growth potency was measured by using WST-8 reagent assay, the absorbance at 450 nm was measured by ELISA using a microplate reader (Model 550; BioRad, Tokyo, Japan).

2. Binding Test by Co-Immunoprecipitation Assay

To examine the cause of inhibition of the specific cell growth of 10/24 peptide, by using co-immunoprecipitation assay, it was identified that 10/24 peptide specifically binds to

TABLE 1

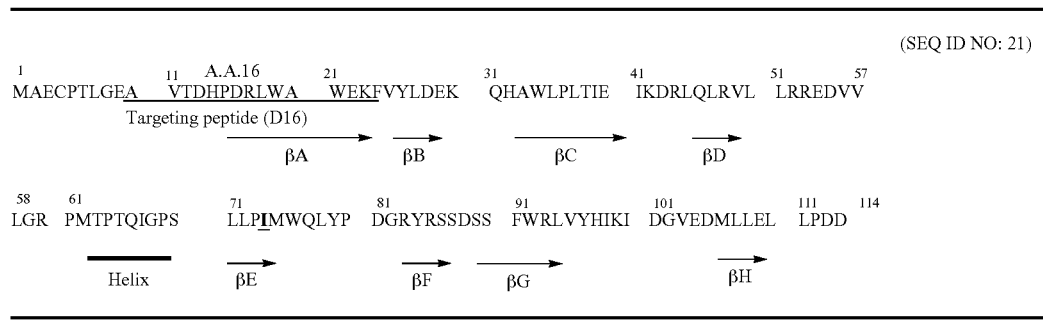

(SEQ ID NO: 21)

Based on the above hypothesis, two peptides, which are a peptide in the vicinity of binding site of the TCL1 and AKT, i.e., a peptide in the vicinity of amino acid residue 10-24 (displays as "10/24") of TCL1, and a control peptide; were produced (Table 2). Peptide were produced by an ordinary peptide synthesizer, and purified by gel filtration or HPLC. Peptides produced by Hokkai BioSystem, and an American company were used.

Figure 7:
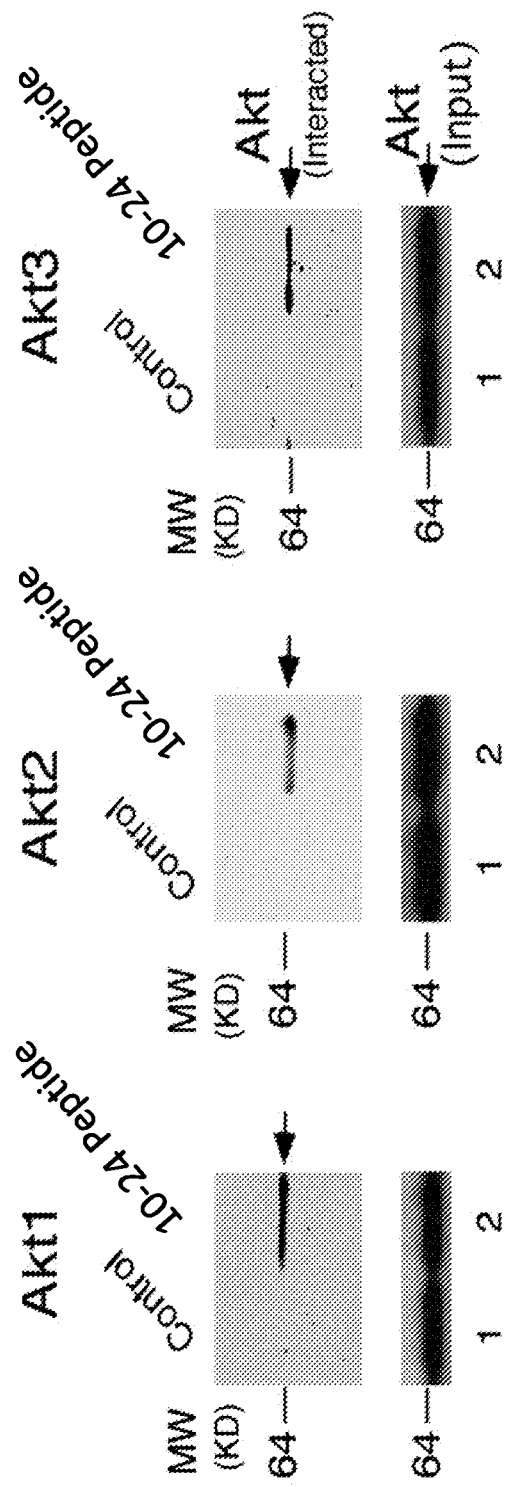
FIG. 7 is a set of pictures showing the results of western blotting after the binding test for 10/24 peptide with Akt subtypes, Akt1, Akt2 and Akt3 molecules, by using co-immunoprecipitation assays, in experiments of the examples of the present invention.

Akt kinase (FIG. 7). In this method, AKT kinase was overexpressed in human 293 cells, and the harvested cell lysates was incubated with 10/24 peptide (NH2-AVTDHPDRL-WAWEKF-COOH) (SEQ ID NO: 1) for around 2 hours. Further, the treated cell lysates were added agarose beads bound to the specific antibody against an epitope that was fused with Akt, and co-incubated for 2-3 hours. Then, molecules adhered in the cell lysates were immunoprecipitated

TABLE 2

```
            Targeting peptides design
                                        (SEQ ID NO: 23)
               NH2-TAT          Flag(DYKDDDDK)-Target Peptides-COOH
               (YGRKKRRQRRR)-

(SEQ ID NO: 24)
10/24 peptide  NH2-YGRKKRRQRRR- DYKDDDDK- AVTDHPDRLWAWEKF     -COOH (SEQ ID NO: 25)
Control Peptide NH2-YGRKKRRQRRR DYKDDDDK- SQAVHAAHEI          -COOH
``` with agarose beads bound to this antibody, and examined the binding to Akt kinase by using western blotting with specific antibody.

2. Lipid-Protein Pull Down Assay

Lipid-protein pull down assay was performed for 10/24 peptide of TCL1.

Figure 8:
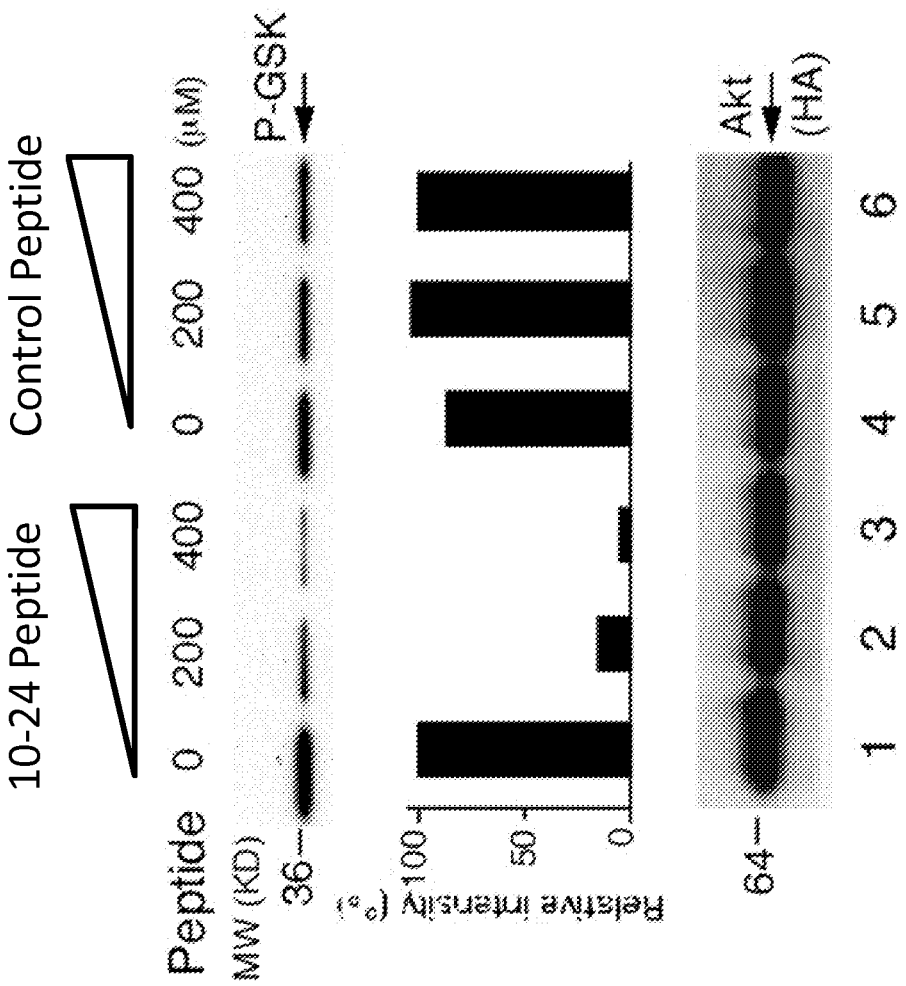
FIG. 8 is a set of pictures showing the results of western blotting after the inhibition tests for Akt activation with 10/24 peptide, by Akt kinase assays with the use of GSK (Glycogen Synthesis Kinase 3) as substrates, in experiments of the examples of the present invention.

Method:

Lipid-protein pull down assay was performed by using PIP Beads (PI (3,4,5) P3 Echelon Bioscience Incorporated). 10/24 NH2-AVTDHPDRLWAWEKF-COOH (SEQ ID NO: 1), and βC NH2-EKQHAWLPLTIE-COOH (SEQ ID NO: 22) as a control, were used. After treatment for 2 hours at 4° C. by using 50 ng of AKT kinase (unactivated, Upstate Biotechnology, #14-279), 25 μl of PIP Beads (PI (3,4,5) P3 Echelon Bioscience Incorporated) was added, then washed with fluid containing (10 mM Hepes, pH7.4, 0.25% NP-40, 140 mM NaCl), and western blotting was performed by using Akt antibody (Cell Signaling) (FIG. 8). In three lanes from the left in the figure, the bindings to AKT were inhibited in a dose-dependent manner at 1-400 μM, while control peptides in right lanes in the figure did not inhibit at all. From these results, it was identified that the peptide (NH2-AVTDHP-DRLWAWEKF-COOH) (SEQ ID NO: 1) competitively inhibits the bindings of Phosphoinositide (PI (3,4,5) P3) to Akt kinase. Thus, this is considered to be the inhibition mechanism for Akt activation.

Example 3

Binding Test Between 10/24 Peptide and Akt Subtype Molecule by Using Co-Immunoprecipitation Assay Binding test between 10/24 peptide and Akt subtype molecule: Akt1, Akt2, or Akt3, was performed by using co-immunoprecipitation assay.

Method:

The cell lysate overexpressed Akt kinase in 293 cells (ATCC) i.e., Akt1, Akt2 or Akt3 in pCMV6 was expressed in 293 cells (ATCC) by using calcium phosphate method, and the overexpressed cells were harvested, lysed, and pre-treated with Protein G/A agarose mixture (50% v/v, ProG/A, Pharmacia). Akt or a control peptide (βC) was added to the cell lysate at 400 μM, inoculated with ProG/A for 3 hours at 4° C., and was added anti Flag M2 antibody (Sigma). The resultant immune precipitant was washed, and then were identified the binding to Akt kinase by western blotting (anti-HA antibody, 3F10, Boehringer Mannheim). The results are shown in FIG. 7. As shown in the figure, the 10/24 peptide bound to any of the three subtypes of molecules, Akt1, Akt2, and Akt3.

Example 4

Inhibition Effect Test for Akt Activation by Akt Kinase Assay with the Use of GSK (Glycogen Synthesis Kinase 3) as Substrate It has been known that Akt promotes phosphorylation of GSK (Glycogen Synthesis Kinase 3).

With the use of the GSK as substrate Akt kinase assay was performed, and inhibition test for Akt activation with 10/24 peptide was performed.

Method:

In vitro Akt kinase assay was performed by using kit (Cell Signaling, #9840). Recombinant Akt protein extracted from mammalian cells was mixed with 200 μM concentrations of peptide, and reacted for 2 hours. Phosphorylation was performed for 4 minutes at 30° C. After analyzing the reaction mixture on SDS gels, GSK phosphorylation was determined by western blotting. The results are shown in FIG. 8. As shown in the FIG. 8, the 10/24 peptide was effectively inhibited the phosphorylation potency for GSK peptide of Akt (three lanes from the left in the figure show the inhibition of GSK phosphorylation diluting the black bands). The similar inhibition effect on Akt kinase activity was also identified by using peptide (NH2-VTDHPDRLWAWEK-RRR-VTDHP-DRLWAWEK-COOH) (SEQ ID NO: 20) having repetitive sequence of 11-23 from 10-24(AVTDHPDRLWAWEKF) (SEQ ID NO: 1).

Example 5

Inhibition Effect Test for Akt Phosphorylation Activation in Mouse Fibrosarcoma Cells (QrSP-11)

Inhibition effect on Akt activation of AKT phosphorylation (serine 473 residue, threonine 308 residue) of 10/24 peptide and control peptide in mouse QrSP-11 fibrosarcoma cells were examined.

Figure 9:
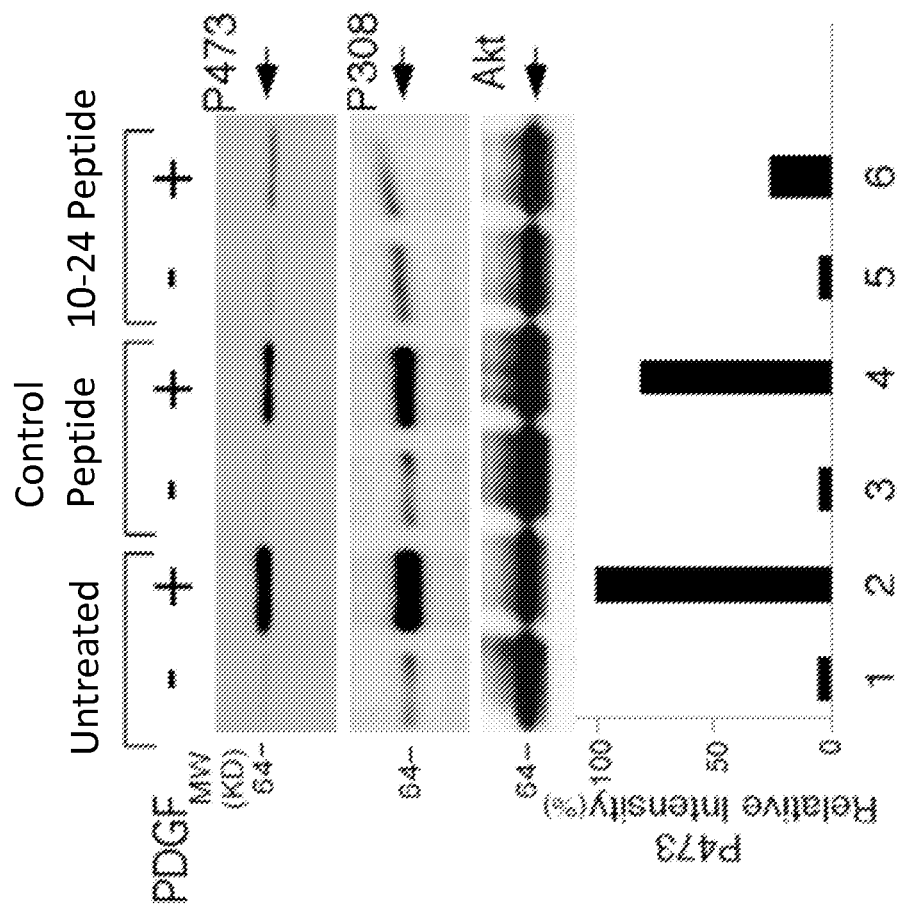
FIG. 9 is a set of pictures showing the results of western blotting with the use of various antibodies for the inhibition effects on the AKT activation of 10/24 peptide in mouse QrSP-11 fibrosarcoma cells and control peptide for phosphorylation (serine 473 residue, threonine 308 residue), in experiments of the examples of the present invention.

Method:

QrSP-11 cells were mixed with 50 mM concentrations of peptide for 16 hours. Then the mixture was stimulated with PDGF (PDGF-AB, Sigma, 3226). The cells were lysed in the presence of phosphatase inhibitor, analyzed on SDS gels, and western blotting was performed by ECL (Amersham) with the use of various antibodies (Cell Signaling; anti-Akt #9272, anti-pThr308 #9275L, and anti-pSer473 #9271L). The results are shown in FIG. 9. As shown in the figure, in the 10/24 peptide treated cells, phosphorylations of both serine473 and threonine308 were inhibited as shown at the right in the figure. That is, phosphorylation inhibition caused by 10/24 peptide was indicated by diluting the black bands at the right compared to the second and forth rows from the left in the figure.

Example 6

Inhibition Effect Test for the Activation and Membrane Translocation of AKT of 10/24 Peptide Inhibition effect for the activation and membrane translocation of AKT of 10/24 peptide were tested with the use of 293 cells (ATCC).

Method:

One mg of AKT was overexpressed in 293 cells (ATCC) with the use of FuGENE6 (Roche Diagnostics). Sixteen hours later the serum was eliminated, and the cells were stimulated with PDGF-AB (Sigma, #3226) for 10 minutes. The cells were fixed with 4% paraformaldehyde, stained with FITC-conjugated anti-HA antibody (12CA5, MBL) or phospho-Ser 473 antibody (587-F11, Cell Signaling), and observed under the confocal microscope (Nikon).

Figure 10:
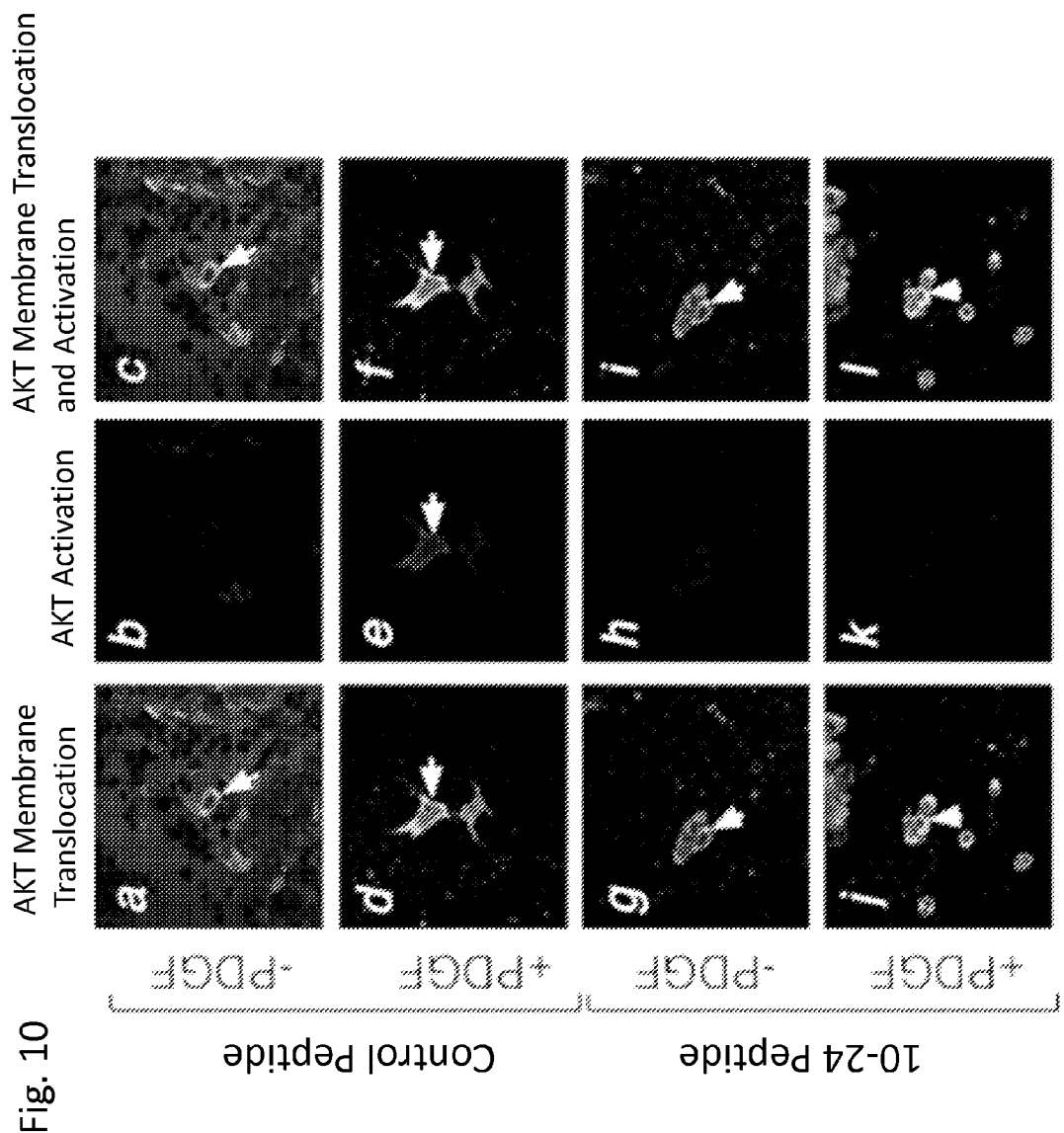
FIG. 10 is a set of pictures observed under the microscope showing the results of examination for the inhibition effects on the membrane translocation and AKT activation of 10/24 peptide with the use of 293 cells (ATCC), in experiments of the example of the present invention.

The results are shown in FIG. 10. As shown in the FIG. 10, in the 10/24 treated cells (g-i), the inhibition of the membrane translocation and activation of AKT was identified compared with the control peptides (a-f) (around the cells glowed green or yellow as shown in d or f, while this effect was inhibited in the 10/24 peptide as shown in j or i. See the figure). That is, from the results of the experiment, it was identified that the 10/24 peptide inhibits the activation at the same time as the translocating of AKT to the membrane in cells. AKT essentially translocates to the cell surface where it is activated, but in the 10/24 peptide treated cells, it was identified that the translocation to membrane and activation of AKT was inhibited.

Example 7

Induction of Apoptosis and Anti-Tumor Effect by 10/24 Peptide

Figure 11:
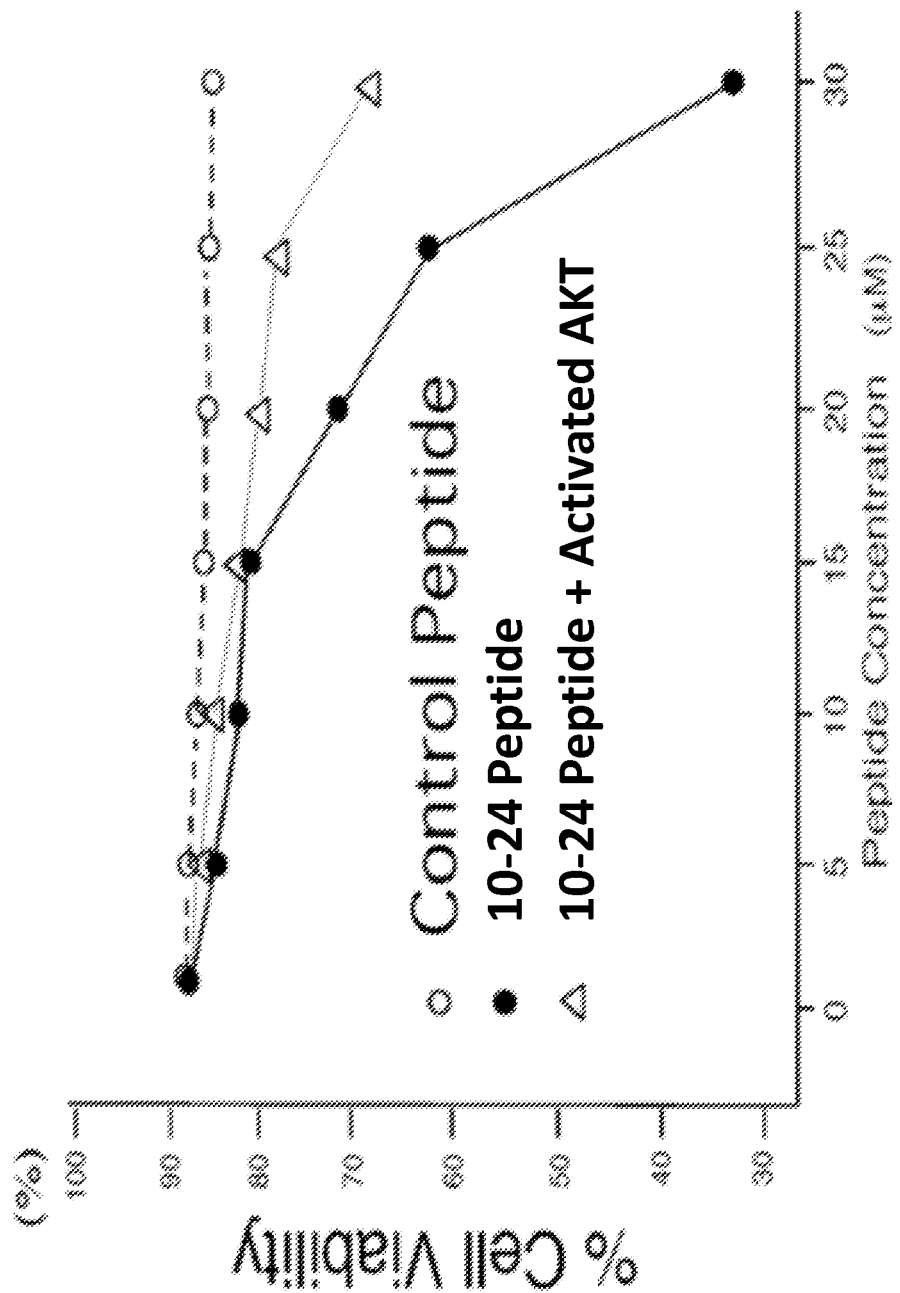
FIG. 11 is a picture showing the results of examination for the effects on apoptosis of 10/24 peptide with the use of human T cell leukemia cells (T4), in experiments of the examples of the present invention.

The effect on apoptosis of 10/24 peptide was examined with the use of human T cell leukemia cells (T4).
Method:
10/24 peptide (NH2-AVTDHPDRLWAWEKF-COOH) (SEQ ID NO: 1) was pre-treated at 0-30 μM concentrations with the use of T4 cell lines without stimulation, 48 hours later stained with propidium iodide, and the apoptosis was determined by FACS (Beckton Dickinson). Further, to identify the AKT dependency of the anti-tumor effect, myr-AKT (constitutively activated AKT) was overexpressed. The results are shown in FIG. 11. As shown in the figure, 10/24 peptide was identified to enhance apoptosis, compared with control peptide. Similar tendency to enhance the apoptosis was also identified during the induction of apoptosis by dexamethasone. As a result of myr-AKT overexpression, apoptosis was inhibited (Δ in FIG. 11), and it was identified that 10/24 peptide achieves the effect in AKT dependent manner.

Example 8

In Vivo Anti-Tumor Effect by 10/24 Peptide

Figure 12:
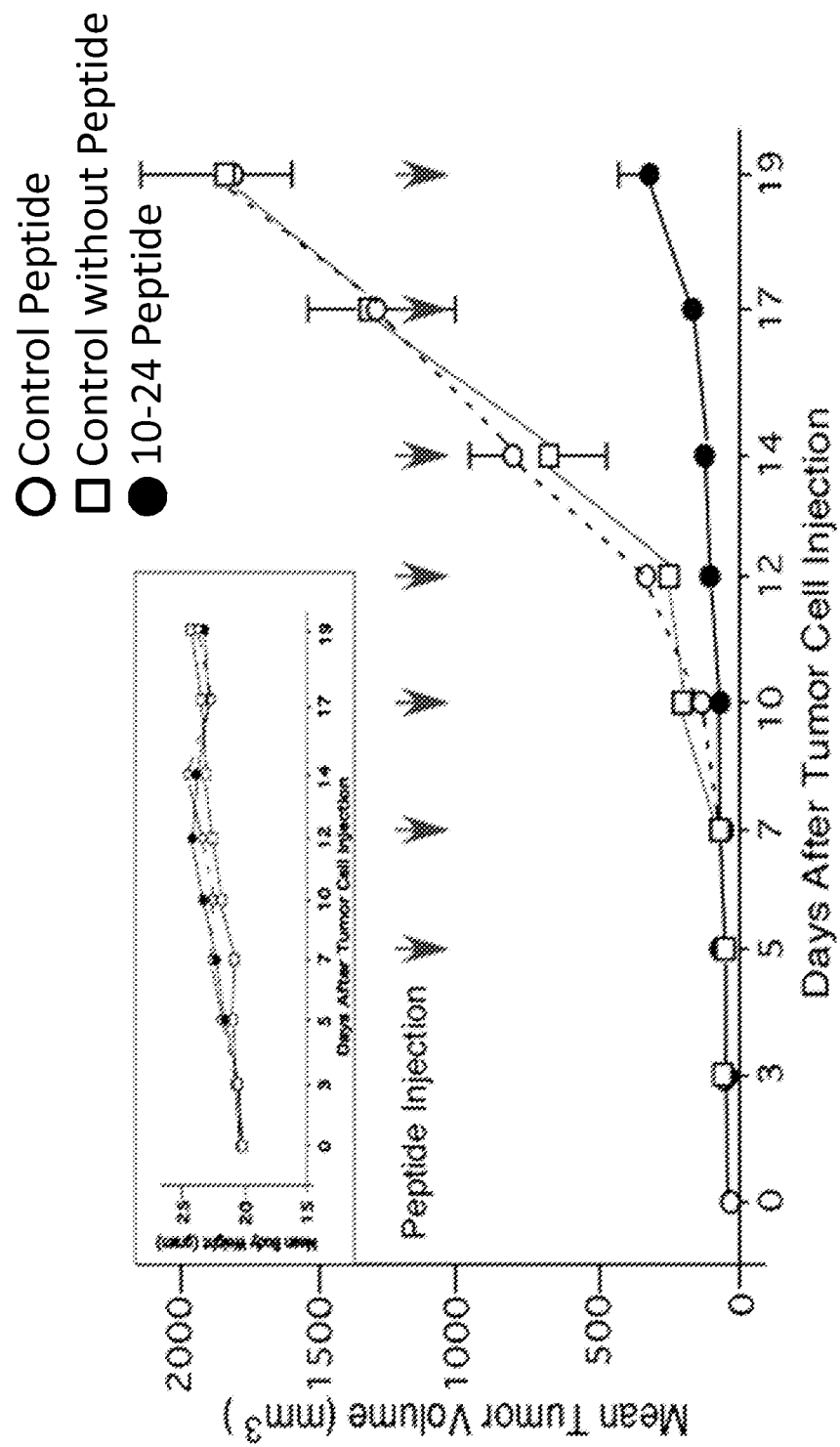
FIG. 12 is a picture showing the results of examination for in vivo anti-tumor effect by 10/24 peptide with the use of transplanted tumor cells, in experiments of the examples of the present invention.

In vivo anti-tumor effect by 10/24 peptide with the use of the transplanted tumor cells was examined.
Method:
Mouse QrSP-11 fibrosarcoma cells was transplanted to abdominal wall of C57BL/6 mouse, and examined the inhibition effect on tumor growth by peptide. 10/24 peptide or control peptide was injected directly into tumor cells (2 μM was administered 3 times a week for each mouse, shown by arrows in the figure), the tumor diameters were measured and the volumes were calculated. The results are shown in FIG. 12. As shown in the figure, it was identified that tumor growth was effectively inhibited in 10/24 peptide.

Example 9

Histological Examination of 10/24 Peptide Treated Mouse Tumor

Figure 13:
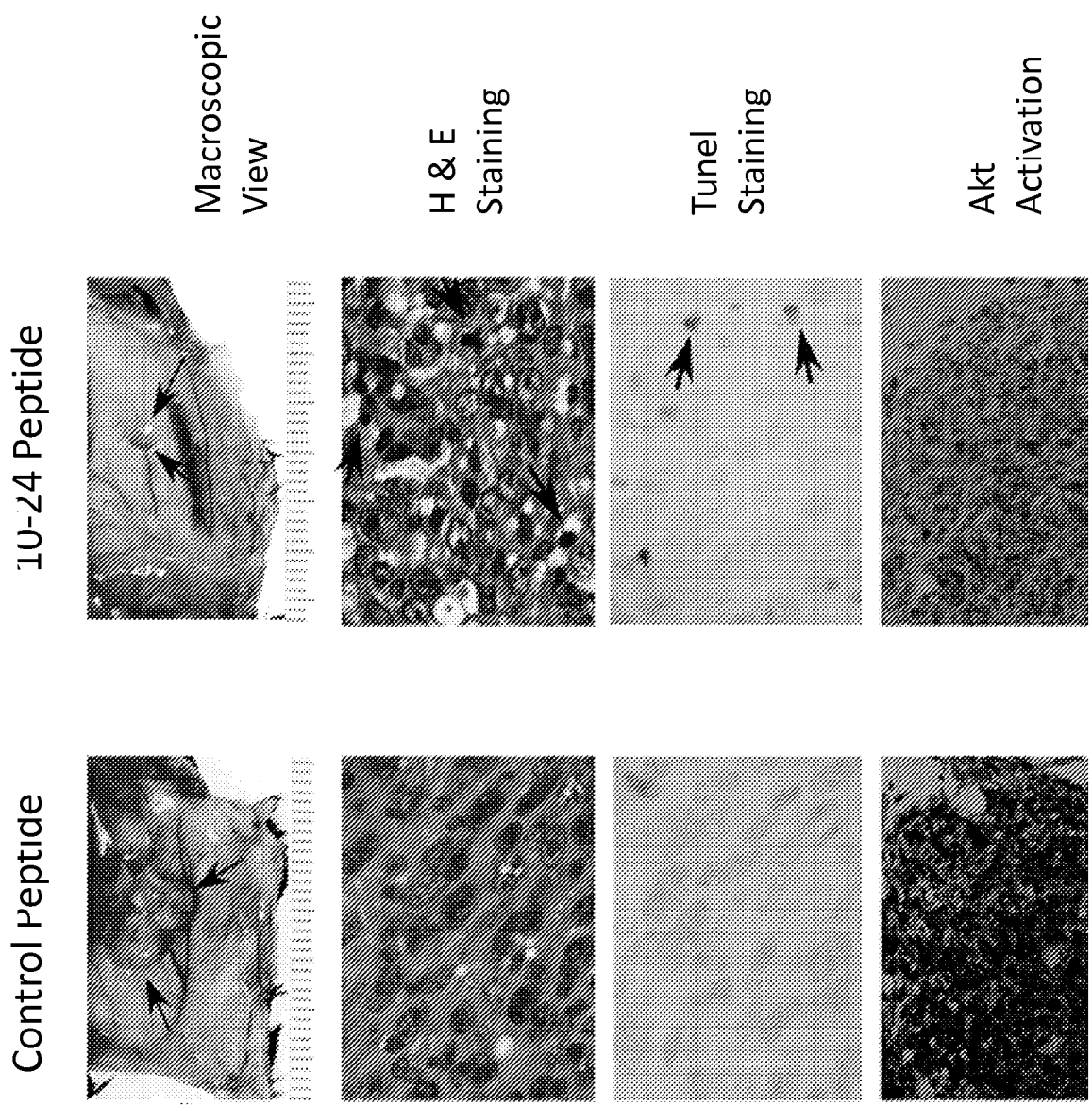
FIG. 13 is a set of pictures showing the results of observations in macroscopic appearance, H&E staining, TUNEL staining, and Akt activation; of the experimental mouse tumors examined in vivo anti-tumor effect by 10/24 peptide that was collected on the day 9, with the use of transplanted tumor cells, in experiments of the examples of the present invention.

Experimental mouse tumors of example 8 were harvested on the day 9, and histologically examined by macroscopic appearance, hematoxylin-eosin (H&E) staining (an observing method for conditions of cell nucleus and the like), TUNEL (Tdt-mediated dUTP nick end labeling, #MK500, Takara) immunostaining (a histologically identifying method for the way of the atypical death of carcinoma i.e., apoptosis), and phospho Akt (Ser473) monoclonal antibody (a method for determining 587F11, Cell Signaling, phosphorylation of AKT kinase, and observing the activation). The results are shown in FIG. 13.

As shown in pictures in the figure, by macroscopic appearance, reduction in tumor size was clearly observed in the 10/24 peptide treated compared to the control; by H&E staining, increased apoptosis was observed in the 10/24 peptide treated; by TUNEL staining, increased cell apoptosis was observed in the 10/24 peptide treated; and by Akt activation, inhibition of Akt activation was observed in the 10/24 peptide treated. That is, by histological examination of the 10/24 peptide treated mouse tumor, it was identified that the 10/24 peptide suppressed tumor growth, increased apoptosis (H&E, TUNEL), and inhibited AKT activity (p473 staining).

The invention claimed is:

1. An isolated polypeptide that specifically inhibits Akt activity consisting of: an amino acid sequence indicated in SEQ ID NO: 1 or 20 of the sequence listing.

2. A composition for inhibiting Akt activity, comprising: the isolated polypeptide according to claim 1 as an active ingredient.

3. A method for inhibiting Act activity in a cell, comprising contacting the cell with the composition according to claim 2, wherein specific inhibition of Akt activity in the cell is the inhibition of binding of phosphoinositide to Akt.

4. A method for treating breast cancer comprising administering to a patient in need thereof a composition of claim 2.

5. A method for treating lung cancer comprising administering to a patient in need thereof a composition of claim 2.

6. A method for treating leukemia comprising administering to a patient in need thereof a composition of claim 2.

7. A method for treating lymphoid tumor comprising administering to a patient in need thereof a composition of claim 2.

8. The composition of claim 2, further comprising a pharmaceutical carrier.

* * * * *

UNITED STATES PATENT AND TRADEMARK OFFICE
CERTIFICATE OF CORRECTION

PATENT NO. : 8,440,630 B2  
APPLICATION NO. : 10/583058  
DATED : May 14, 2013  
INVENTOR(S) : Masayuki Noguchi et al.

Page 1 of 1

It is certified that error appears in the above-identified patent and that said Letters Patent is hereby corrected as shown below:

In the Claims

At col. 25, line 41 (claim 1) the words "indicated in" should be deleted;

At col. 25, line 41 (claim 1) the ":" should be deleted;

At col. 25, line 41 (claim 1) the word "sequence" should be replaced with
-- sequence: --;

At col. 25, line 42 (claim 1) after the word "or" -- SEQ ID NO: -- should be entered
and the words "of the sequence listing" should be deleted;

At col. 25, line 43 (claim 2) the "," should be deleted;

At col. 25, line 44 (claim 2) the words "according to" should be deleted and the
word -- of -- should be inserted before the word "claim";

At col. 25, line 46 (claim 3) the letters "Act" should be replaced with the letters
-- Akt --;

At col. 25, line 47 (claim 3) the words "according to" should be deleted and the
word -- of -- should be inserted before the word "claim".

Signed and Sealed this
Twenty-fourth Day of September, 2013

Teresa Stanek Rea
*Deputy Director of the United States Patent and Trademark Office*

SEQUENCE LISTING

```
<160> NUMBER OF SEQ ID NOS: 25

<210> SEQ ID NO 1
<211> LENGTH: 15
<212> TYPE: PRT
<213> ORGANISM: Homo sapiens

<400> SEQUENCE: 1

Ala Val Thr Asp His Pro Asp Arg Leu Trp Ala Trp Glu Lys Phe
1               5                   10                  15

<210> SEQ ID NO 2
<211> LENGTH: 45
<212> TYPE: DNA
<213> ORGANISM: Homo sapiens

<400> SEQUENCE: 2
gcagtcaccg accacccgga ccgcctgtgg gcctgggaga agttc                45

<210> SEQ ID NO 3
<211> LENGTH: 30
<212> TYPE: PRT
<213> ORGANISM: Homo sapiens

<400> SEQUENCE: 3
```

```
Met Ala Ser Glu Ala Ser Val Arg Leu Gly Val Pro Pro Gly Arg Leu
1               5                   10                  15

Trp Ile Gln Arg Pro Gly Ile Thr Glu Asp Glu Glu Arg
            20                  25                  30

<210> SEQ ID NO 4
<211> LENGTH: 90
<212> TYPE: DNA
<213> ORGANISM: Homo sapiens

<400> SEQUENCE: 4
atggcctccg aagcttctgt gcgtctaggg gtgccccctg gccgtctgtg gatccagagg      60
cctggcatct acgaagatga ggagggaga                                       90

<210> SEQ ID NO 5
<211> LENGTH: 25
<212> TYPE: PRT
<213> ORGANISM: Homo sapiens

<400> SEQUENCE: 5

Met Ala Gly Glu Asp Val Gly Ala Pro Pro Asp His Leu Thr Val His
1               5                   10                  15

Gln Glu Gly Ile Tyr Arg Asp Glu Tyr
            20                  25

<210> SEQ ID NO 6
<211> LENGTH: 75
<212> TYPE: DNA
<213> ORGANISM: Homo sapiens

<400> SEQUENCE: 6
atggcaggag aggatgtggg ggctccaccc gatcacctct gggttcacca agagggtatc      60
taccgcgacg aatac                                                      75

<210> SEQ ID NO 7
<211> LENGTH: 16
<212> TYPE: PRT
<213> ORGANISM: mouse

<400> SEQUENCE: 7

Ala Glu Thr Pro Ala His Pro Asn Arg Leu Trp Ile Trp Glu Lys His
1               5                   10                  15

<210> SEQ ID NO 8
<211> LENGTH: 48
<212> TYPE: DNA
<213> ORGANISM: Mouse

<400> SEQUENCE: 8
gcagagacac ctgcacaccc caaccgcctg tggatctggg agaagcac                  48

<210> SEQ ID NO 9
<211> LENGTH: 16
<212> TYPE: PRT
<213> ORGANISM: rat

<400> SEQUENCE: 9

Pro Glu Thr Pro Pro His Pro Asp Arg Leu Trp Leu Trp Glu Lys His
1               5                   10                  15

<210> SEQ ID NO 10
<211> LENGTH: 48
<212> TYPE: DNA
```

<213> ORGANISM: mouse

<400> SEQUENCE: 10
ccagagacac ccccacaccc cgaccgcctg tggctctggg agaagcac             48

<210> SEQ ID NO 11
<211> LENGTH: 33
<212> TYPE: DNA
<213> ORGANISM: Homo sapiens

<400> SEQUENCE: 11
ccaccaaacc caaaaaaaga gatcgaattc atg                             33

<210> SEQ ID NO 12
<211> LENGTH: 33
<212> TYPE: DNA
<213> ORGANISM: Homo sapiens

<400> SEQUENCE: 12
attcatagat ctctgcaggt cgacggatcc tca                             33

<210> SEQ ID NO 13
<211> LENGTH: 60
<212> TYPE: DNA
<213> ORGANISM: Homo sapiens

<400> SEQUENCE: 13
atggccgagt gcccgacact cggggaggca gtcaccgacc acccgggccg cctgtgggcc    60

<210> SEQ ID NO 14
<211> LENGTH: 33
<212> TYPE: DNA
<213> ORGANISM: Homo sapiens

<400> SEQUENCE: 14
gtgtatttgg acgagatgca gcacgcctgg ctg                             33

<210> SEQ ID NO 15
<211> LENGTH: 34
<212> TYPE: DNA
<213> ORGANISM: Homo sapiens

<400> SEQUENCE: 15
gataaaggat aggttacggt tacgggtgct cttg                            34

<210> SEQ ID NO 16
<211> LENGTH: 33
<212> TYPE: DNA
<213> ORGANISM: Homo sapiens

<400> SEQUENCE: 16
ccaagcctgc tgcctgtcat gtggcagctc tac                             33

<210> SEQ ID NO 17
<211> LENGTH: 49
<212> TYPE: DNA
<213> ORGANISM: Homo sapiens

<400> SEQUENCE: 17
atcatcggat cctcagtcat ctggcagcag ctcgagaagc acgtcctcc             49

<210> SEQ ID NO 18
<211> LENGTH: 39
<212> TYPE: DNA

<213> ORGANISM: Homo sapiens

<400> SEQUENCE: 18
cagcacgcct ggctggccgc ggccatcgag ataaaggat                                    39

<210> SEQ ID NO 19
<211> LENGTH: 24
<212> TYPE: DNA
<213> ORGANISM: Homo sapiens

<400> SEQUENCE: 19
gcctggctgg ccttaatcga gata                                                    24

<210> SEQ ID NO 20
<211> LENGTH: 29
<212> TYPE: PRT
<213> ORGANISM: Homo sapiens

<400> SEQUENCE: 20

Val Thr Asp His Pro Asp Arg Leu Trp Ala Trp Glu Lys Arg Arg
1               5                   10                  15

Val Thr Asp His Pro Asp Arg Leu Trp Ala Trp Glu Lys
            20                  25

<210> SEQ ID NO 21
<211> LENGTH: 114
<212> TYPE: PRT
<213> ORGANISM: Homo sapiens

<400> SEQUENCE: 21

Met Ala Glu Cys Pro Thr Leu Gly Glu Ala Val Thr Asp His Pro Asp
1               5                   10                  15

Arg Leu Trp Ala Trp Glu Lys Phe Val Tyr Leu Asp Glu Lys Gln His
            20                  25                  30

Ala Trp Leu Pro Leu Thr Ile Glu Ile Lys Asp Arg Leu Gln Leu Arg
        35                  40                  45

Val Leu Leu Arg Arg Glu Asp Val Val Leu Gly Arg Pro Met Thr Pro
    50                  55                  60

Thr Gln Ile Gly Pro Ser Leu Leu Pro Ile Met Trp Gln Leu Tyr Pro
65                  70                  75                  80

Asp Gly Arg Tyr Arg Ser Ser Asp Ser Ser Phe Trp Arg Leu Val Tyr
                85                  90                  95

His Ile Lys Ile Asp Gly Val Glu Asp Met Leu Leu Glu Leu Leu Pro
            100                 105                 110

Asp Asp

<210> SEQ ID NO 22
<211> LENGTH: 12
<212> TYPE: PRT
<213> ORGANISM: Homo sapiens

<400> SEQUENCE: 22

Glu Lys Gln His Ala Trp Leu Pro Leu Thr Ile Glu
1               5                   10

<210> SEQ ID NO 23
<211> LENGTH: 22
<212> TYPE: PRT
<213> ORGANISM: Artificial Sequence
<220> FEATURE:
<223> OTHER INFORMATION: Target peptid -continued

```
<400> SEQUENCE: 23

Thr Ala Thr Tyr Gly Arg Lys Lys Arg Arg Gln Arg Arg Asp Tyr
1               5                   10                  15

Lys Asp Asp Asp Asp Lys
            20

<210> SEQ ID NO 24
<211> LENGTH: 34
<212> TYPE: PRT
<213> ORGANISM: Artificial Sequence
<220> FEATURE:
<223> OTHER INFORMATION: 10/24 peptide

<400> SEQUENCE: 24

Tyr Gly Arg Lys Lys Arg Arg Gln Arg Arg Asp Tyr Lys Asp Asp
1               5                   10                  15

Asp Asp Lys Ala Val Thr Asp His Pro Asp Arg Leu Trp Ala Trp Glu
            20                  25                  30

Lys Phe

<210> SEQ ID NO 25
<211> LENGTH: 29
<212> TYPE: PRT
<213> ORGANISM: Artificial Sequence
<220> FEATURE:
<223> OTHER INFORMATION: Control peptide

<400> SEQUENCE: 25

Tyr Gly Arg Lys Lys Arg Arg Gln Arg Arg Asp Tyr Lys Asp Asp
1               5                   10                  15

Asp Asp Lys Ser Gln Ala Val His Ala Ala His Glu Ile
            20                  25
```